United States Patent
Gao et al.

(10) Patent No.: US 9,517,272 B2
(45) Date of Patent: Dec. 13, 2016

(54) TEMPERATURE DEPENDENT ACTIVATION OF CATALYTIC NUCLEIC ACIDS FOR CONTROLLED ACTIVE SUBSTANCE RELEASE

(75) Inventors: Jiang Gao, Berlin (DE); Monika Fischler, Berlin (DE); Volker A. Erdmann, Berlin (DE)

(73) Assignee: MAGFORCE AG, Berlin (DE)

( * ) Notice: Subject to any disclaimer, the term of this patent is extended or adjusted under 35 U.S.C. 154(b) by 434 days.

(21) Appl. No.: 13/515,173

(22) PCT Filed: Dec. 16, 2010

(86) PCT No.: PCT/EP2010/007702
§ 371 (c)(1),
(2), (4) Date: Sep. 26, 2012

(87) PCT Pub. No.: WO2011/082796
PCT Pub. Date: Jul. 14, 2011

(65) Prior Publication Data
US 2013/0102545 A1    Apr. 25, 2013

Related U.S. Application Data

(60) Provisional application No. 61/282,471, filed on Feb. 16, 2010.

(30) Foreign Application Priority Data

Dec. 16, 2009    (DE) .................. 10 2009 058 769

(51) Int. Cl.
| C07H 21/04 | (2006.01) |
| C07H 21/02 | (2006.01) |
| A61K 47/48 | (2006.01) |
| A61K 9/00 | (2006.01) |
| A61K 9/16 | (2006.01) |
| A61K 9/51 | (2006.01) |
| A61K 41/00 | (2006.01) |

(52) U.S. Cl.
CPC ....... *A61K 47/48138* (2013.01); *A61K 9/0009* (2013.01); *A61K 9/1676* (2013.01); *A61K 9/513* (2013.01); *A61K 41/0028* (2013.01); *A61K 47/48092* (2013.01); *A61K 47/48861* (2013.01)

(58) Field of Classification Search
None
See application file for complete search history.

(56) References Cited

U.S. PATENT DOCUMENTS

| 6,048,515 A | 4/2000 | Kresse et al. |
| 6,183,658 B1 | 2/2001 | Lesniak et al. |
| 6,348,185 B1 * | 2/2002 | Piwnica-Worms ......... A61K 47/48338 424/1.11 |
| 6,541,039 B1 | 4/2003 | Lesniak et al. |
| 6,605,713 B1 | 8/2003 | Furste et al. |
| 2001/0011151 A1 | 8/2001 | Feucht |
| 2001/0012912 A1 | 8/2001 | Feucht |
| 2003/0219422 A1 | 11/2003 | Frauendorf et al. |
| 2007/0148437 A1 | 6/2007 | Müller-Schulte |
| 2008/0268061 A1 | 10/2008 | Jordan et al. |
| 2011/0052609 A1 | 3/2011 | Waldoefner et al. |
| 2011/0160515 A1 | 6/2011 | Feucht et al. |
| 2011/0223255 A1 | 9/2011 | Thiesen et al. |
| 2012/0149763 A1 | 6/2012 | Erdmann et al. |

FOREIGN PATENT DOCUMENTS

| DE | 10 2008 008 522 A1 | 8/2009 | |
| DE | 10 2009 058 769.1 | * 12/2009 | |
| DE | 10 2009 007 929 A1 | 8/2010 | |
| WO | WO 97/38058 A1 | 10/1997 | |
| WO | WO 98/58673 A1 | 12/1998 | |
| WO | WO 01/10500 A1 | 2/2001 | |
| WO | WO 01/10501 A1 | 2/2001 | |
| WO | WO 03/060142 A2 | 7/2003 | |
| WO | WO 03/106625 A2 | 12/2003 | |
| WO | WO 2005/042142 A2 | 5/2005 | |
| WO | WO 2005/070471 A2 | 8/2005 | |
| WO | WO 2005111238 | * 11/2005 | ............... C12Q 1/68 |
| WO | WO 2006/108405 A2 | 10/2006 | |
| WO | WO 2008/073851 A2 | 6/2008 | |
| WO | WO 2009/086824 A2 | 7/2009 | |
| WO | WO 2009/100716 A2 | 8/2009 | |
| WO | WO 2009/118091 A1 | 10/2009 | |
| WO | WO 2012/089207 A2 | 7/2012 | |

OTHER PUBLICATIONS

Williams et al (Proc. Natl. Acad. Sci. USA vol. 94, pp. 11285-11290, Oct. 1997).*
Hauser et al (Nucleic Acids Research, 2006, vol. 34, No. 18 5101-5111).*
http://en.wikipedia.org/wiki/Hammerhead_ribozyme, retrieved from the web on Jun. 8, 2015.*
Abu et al., "In vitro and in vivo study of an albumin-binding prodrug of doxorubicin that is cleaved by cathepsin B," *Cancer Chemother Pharmacol.*, 64, 413-8. Epub Feb. 20, 2009.

(Continued)

*Primary Examiner* — Richard Schnizer
(74) *Attorney, Agent, or Firm* — The Marbury Law Group, PLLC

(57) ABSTRACT

The present invention relates to an active substance release system containing two compounds. The first compound comprises a nanoparticle, combined with an oligonucleotide inhibition strand that is hybridized with a catalytically active nucleic acid. The second compound comprises a carrier, combined with a substrate molecule that is coupled to a therapeutic active substance. By means of external stimulation, the catalytically active nucleic acid of the first compound is released and specifically binds to the substrate molecule of the second compound. This leads to cleavage of the substrate molecule, whereby the active substance bound thereto is released.

30 Claims, 6 Drawing Sheets

(56) References Cited

OTHER PUBLICATIONS

Figure 1:
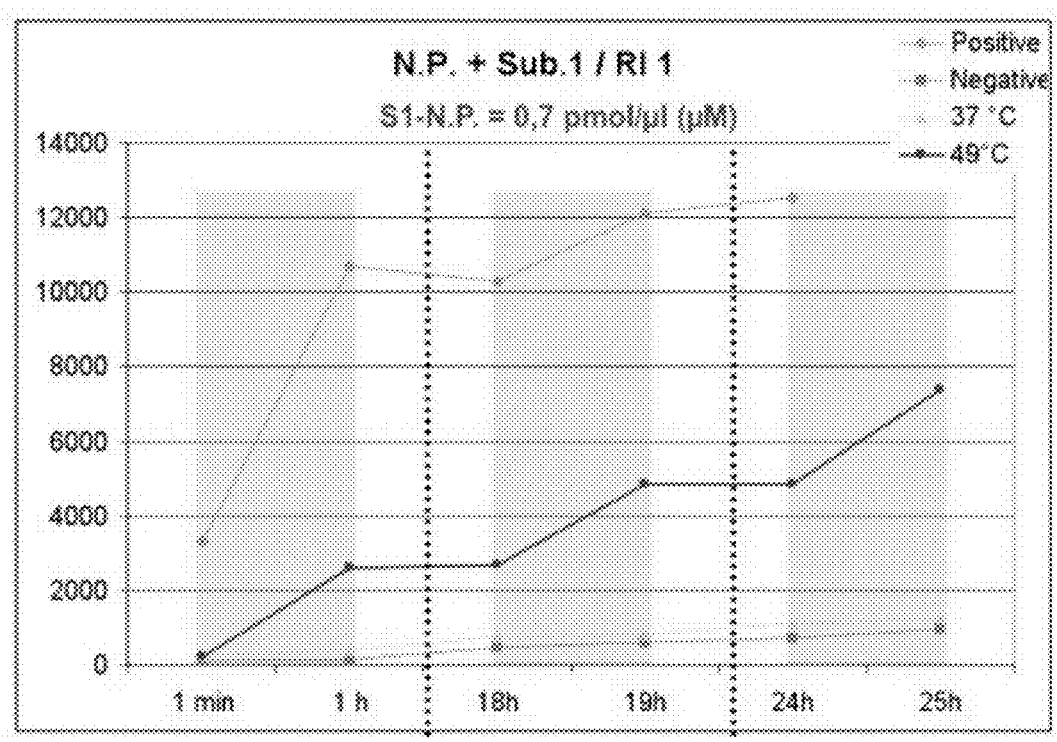

Boga et al., "Characterisation of the conjugate of the (6-maleimidocaproyl)hydrazone derivative of doxorubicin with lactosaminated human albumin by 13C NMR spectroscopy; Development of enzymatically cleavable prodrugs derived from dendritic polyglycerol; In vitro and in vivo study of an albumin-binding prodrug of doxorubicin that is cleaved by cathepsin B," Eur J Pharm Sci., 38, 262-9. Epub Aug. 18, 2009.

Calderon et al., "Development of enzymatically cleavable prodrugs derived from dendritic polyglycerol; In vitro and in vivo study of an albumin-binding prodrug of doxorubicin that is cleaved by cathepsin B," Bioorg Med Chem Lett., 19, 3725-8. Epub May 18, 2009.

Carmi et al., "Cleaving DNA with DNA; Catalytic nucleic acids: from lab to applications," Proc Natl Acad Sci U S A, 1998, 95, 2233-7.

Karkare et al., "Promising nucleic acid analogs and mimics: characteristic features and applications of PNA, LNA, and morpholino," Appl Microbiol Biotechnol., 71, 575-86. Epub May 9, 2006.

Klussmann et al., "Mirror-image RNA that binds D-adenosine; Thiophosphate interference experiments locate phosphates important for the hammerhead RNA self-cleavage reaction," Nat Biotechnol., 1996, 14, 1112-5.

Kratz et al., "Albumin as a drug carrier: design of prodrugs, drug conjugates and nanoparticles; Characterisation of the conjugate of the (6-maleimidocaproyl)hydrazone derivative of doxorubicin with lactosaminated human albumin by 13C NMR spectroscopy; Development of enzymatically cleavable prodrugs derived from dendritic polyglycerol; In vitro and in vivo study of an albumin-binding prodrug of doxorubicin that is cleaved by cathepsin B," J Control Release., 132, 171-83. Epub May 17, 2008.

Liu et al., "Colorimetric biosensors based on DNAzyme-assembled gold nanoparticles," J Fluoresc, 2004, 14(4): 343-54.

Ogawa et al., "Easy design of logic gates based on aptazymes and noncrosslinking gold nanoparticle aggregation," Chem Commun, 2009, (Camb)(31): 4666-8.

Patil et al., "DNA-based therapeutics and DNA delivery systems: a comprehensive review," AAPS J, 2005, 7(1): E61-77.

Perrault et al., "Identification of Hammerhead Ribozymes in All Domains of Life Reveals Novel Structural Variations", PLOS Computational Biology, vol. 7, No. 5, May 2011.

Ruffner et al., "Thiophosphate interference experiments locate phosphates important for the hammerhead RNA self-cleavage reaction," Nucleic Acids Res., 1990, 18, 6025-9.

Santoro et al., "A general purpose RNA-cleaving DNA enzyme; Cleaving DNA with DNA; Catalytic nucleic acids: from lab to applications," Proc Natl Acad Sci U S A., 1997, 94, 4262-6.

Seelig et al., "Enantioselective Ribozyme Catalysis of a Bimolecular Cycloaddition Reaction This work was supported by the Deutsche Forschungsgemeinschaft (Grant No. Ja 794/3-1) and the Bundesministerium fur Bildung und Forschung (Grant No. BEO 0311861). We thank Dr. S. Klussmann and Dr. S. Vonhoff (Noxxon Pharma AG, Berlin) for the synthesis of the L-ribozyme," Angew Chem Int Ed Engl., 2000, 39, 4576-4579.

Tan et al., "DNAzyme delivery systems: getting past first base," Expert Opin Drug Deliv, 2009, 6(2): 127-38.

Venkatesh et al., "Nucleic acid therapeutic carriers with on-demand triggered release," Bioconjug Chem, 2009, 20(9): 1773-82.

Zhang et al., "Self-assembled gold nanocrystal micelles act as an excellent artificial nanozyme with ribonuclease activity," J Biol Inorg Chem, 2009, 14(5): 653-62.

Zhang et al., "Imaging and cell targeting characteristics of magnetic nanoparticles modified by a funtionalizable zwitterionic polymer with adhesive 3,4-dihydroxyphenyl-$_L$-alanine linkages," Biomaterials, 2010, 31:6582-6588.

Zhang, H., "Quantum dot-A10 RNA aptamer-doxorubicin conjugate." Molecular Imaging and Contrast Agent Database (MICAD), 2008, DOI: NBK23117 [bookaccession], Bethesda (MD): National Center for Biotechnology Information (US); 2004-2012.

Zhang, H., "Thermally cross-linked superparamagnetic iron oxide nanoparticle-A10 RNA aptamer-doxorubicin conjugate," Molecular Imaging and Contrast Agent Database (MICAD), 2008, DOI: NBK23367 [bookaccession], Bethesda (MD): National Center for Biotechnology Information (US); 2004-2012.

Zhou et al., "Cooperative binding and self-assembling behavior of cationic low molecular-weight dendrons with RNA molecules," Org Biomol Chem. 2006, 4(3): 581-5.

International Search Report and Written Opinion mailed Feb. 23, 2012 in International Application No. PCT/EP2010/007702.

Handbook "Nucleic Acids from A to Z", Sabine Müller (Ed.), Wiley-VCH Verlag GmbH & Co KGaA, 2008, pp. 130 bis 132, 248 and 249.

A.M. Prochorov (ed.); Great Soviet Encyclopedia, vol. 10, p. 179, col. 524, Moscow, 1972 (with English translation of excerpt), Translated excerpt only.

* cited by examiner

SEQUENCE LISTING

```
<160> NUMBER OF SEQ ID NOS: 5

<210> SEQ ID NO 1
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
ggcucgacug augaggcgc                                                  19

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gcctcatcag tcgagcc                                                    17

<210> SEQ ID NO 3
<211> LENGTH: 24
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 3
gcgccgaaac accgugucuc gagc                                              24

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gcgcctcatc agtcgagcc                                                    19

<210> SEQ ID NO 5
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
gcgccgaaac accguguc                                                     18
```

TEMPERATURE DEPENDENT ACTIVATION OF CATALYTIC NUCLEIC ACIDS FOR CONTROLLED ACTIVE SUBSTANCE RELEASE

SEQUENCE LISTING

The instant application contains a Sequence Listing which has been submitted in ASCII format via EFS-Web and is hereby incorporated by reference in its entirety. Said ASCII copy, created on Dec. 10, 2012, is named 98567115.txt and is 1,640 bytes in size.

The present invention concerns an active substance release system that operates by means of a catalytically active nucleic acid. In the first step, the catalytically active nucleic acid is released by an external stimulus from an oligonucleotide inhibition strand bonded to a nanoparticle. The released active nucleic acid bonds in the second step to its substrate, a nanoparticle-active substance conjugate, causing a covalently, electrostatically, coordinatively, or ionically bonded substance or an intercalated active substance to be released.

Patent Application WO2006/108405, which is deemed the closest prior art, concerns nanoparticles wherein a therapeutically active substance is bonded to said particles, and wherein the release of the therapeutically active substance from the nanoparticles is brought about or initiated by an alternating magnetic field. However, it has been found that direct thermal release of the active substance from the nanoparticles is often not sufficiently effective to achieve a therapeutically effective concentration of the released active substance, e.g. in tumor cells, with only relatively small increases in temperature.

The purpose of the present invention is to provide a process, and suitable compounds with coupled active substances for use in this process, that makes it possible to achieve quantitative release of the active substance with only slight increases in temperature, and thus further increases efficacy compared to the process disclosed in WO2006/108405.

The present invention achieves this purpose by providing an active substance release system containing a Compound 1 and a Compound 2, wherein said Compound 1 is activated by the temperature-induced release of a catalytically active nucleic acid, and wherein the catalytically active nucleic acid in turn catalytically releases the active substance from the second compound. As shown in the examples, this is carried out using e.g. an L-RNA as a catalytically active nucleic acid, wherein the catalytically active nucleic acid is hybridized under physiological conditions with an L-DNA in the form of an inhibitor. This complex has been found in a stability test to be stable in human serum. By using L-nucleic acids, interactions with native (e.g. endogenous) nucleases occurring in the target organism can also be eliminated. By modifying the base sequence and length of the oligonucleotide inhibition strand, the melting point of the conjugate bonded to the particle is adjusted such that no dehybridization occurs under physiological conditions (shown in the present invention as 38° C., i.e. slightly higher than normal body temperature). At body temperature, the double strands are sufficiently stable to fully inhibit the catalytic nucleic acids. If the particle is heated, however, e.g. by means of magnetic induction in an alternating magnetic field, the catalytic nucleic acids of the inhibitor DNA undergo dehybridization, which leads to release of the double strand, and catalytically active nucleic acids are released. These can be enzymatically cleaved by a second compound containing a carrier that is bonded to a therapeutically active substance via a molecule that functions as a substrate for the catalytic nucleic acid. The active substance is released by this cleavage and can therefore exert its action.

The present invention thus concerns, in a first embodiment, an active substance release system containing a Compound 1 comprising at least one nanoparticle bonded to an oligonucleotide inhibition strand, wherein the oligonucleotide inhibition strand is hybridized with a catalytically active nucleic acid, and a Compound 2 containing a carrier bonded to at least one substrate molecule, wherein the substrate molecule is bonded to at least one therapeutically active substance, wherein the therapeutically active substance can be released by cleavage of the substrate molecule, and wherein cleavage of the substrate molecules takes place via the catalytically active nucleic acid.

The present invention thus specifically concerns an active substance release system comprising a nanoparticle that is bonded to an oligonucleotide inhibition strand, wherein the oligonucleotide inhibition strand is hybridized with a catalytically active nucleic acid, and a further nanoparticle that is bonded to a substrate oligonucleotide, wherein the substrate oligonucleotide is bonded to a therapeutically active substance that can be released by cleavage of the substrate oligonucleotide by the catalytically active nucleic acid.

DEFINITIONS

The term "specifically" is to be understood to mean that the catalytically active nucleic acid preferably acts only on the substrate oligonucleotide and cleaves it, showing no activity with respect to other oligonucleotides.

The term "physiological conditions" is to be understood as referring to the physicochemical conditions present intracellularly or extracellularly in the target tissue in question in the target body, preferably the human body.

The term "essentially no cleavage of the active substance" is to be understood to mean that the active substance, released in a small amount, causes no adverse reactions in the target tissue. This specifically means that over a period of 4 hours (h), less than 10%, more preferably less than 1%, and specifically less than 0.5% of the active substance used in a release experiment, such as e.g. Example 3A, is released.

The terms "catalytic nucleic acids" or "catalytically active nucleic acids" are to be understood as referring to nucleic acid molecules such as "DNAzymes," ribozymes, modified nucleic acids, as well as nucleic acid analogs, which can catalyze specific chemical reactions without the involvement of a protein component. For this process, not only naturally occurring catalytic nucleic acids may be used, but also nucleic acids produced by an evolutive process (e.g. SELEX). Moreover, the catalytic nucleic acids can be produced by means of automated solid phase synthesis.

The term "brought about or initiated by an alternating magnetic field" is to be understood to mean that either the alternating magnetic field and/or the pulses directly cause the release and/or detachment, or the release and/or detachment is brought about indirectly, for example via enzyme activation or heat production.

The term "completely hybridized" is understood to mean that all of the molecules of the catalytically active nucleic acid used are present in a hybridized state. As an excess number of inhibitor strands should preferably be used as claimed in the invention, oligonucleotide inhibitor strands may be present in free form after complete hybridization.

The term "approx." is understood to refer to a deviation of ±5%, specifically ±1%.

The present invention specifically concerns an active substance release system in which the oligonucleotide inhibition strand is covalently bonded, more specifically via a crosslinker (Linker 1), to the nanoparticle.

Linker 1, as well as the subsequently incorporated Linker 2 and Linker 3, can either be covalently formed directly from two functional groups between the nanoparticle (or carrier) and the oligonucleotide. This should preferably consist of a peptide bond, a triazole ring, or a dithiol bridge, or should be produced by means of other dimerization, condensation, alkylation, or Click reactions. They may also consist of homo- or hetero-bifunctional crosslinkers that are inserted between a functional group of the oligonucleotide and a functional group or the reactive surface of the nanoparticle (or carrier). For this purpose, it may be necessary to provide the required functional group that is used for coupling of the oligonucleotide by using a modified nucleotide in oligonucleotide synthesis. This modified nucleotide should preferably be incorporated terminally into the oligonucleotide.

The crosslinker used cannot be cleaved under physiological conditions.

Different groups of crosslinkers may be distinguished for Linker 1, Linker 2, and Linker 3 according to the invention depending on the reactive groups they carry. The heterobifunctional crosslinkers have two different reactive ends, which makes it possible to carry out conjugation sequentially, thus preventing undesirable intramolecular side reactions. Examples of compounds belonging to the group of heterobifunctional crosslinkers include sulfo-SMCC (Succinimidyl-4-(N-maleimido-methyl)cyclohexane-1-carboxylate), sulfo-NHS (-hydroxysulfosuccinimide), EDC (1-ethyl-3-[3-dimethylaminopropyl]carbodiimide hydrochloride), or sulfo-LC-SPDP (N-succinimidyl-3-(2-pyridyldithio)-propionate).

Specifically, using the crosslinker sulfo-SMCC or sulfo-GMBS on the nanoparticle surface, amino groups incorporated by aminosilane modification are reacted with an SH group at the 5'-terminal of the inhibitor oligonucleotide.

In the active substance release system according to the invention, Compound 1 contains the catalytically active nucleic acid and the oligonucleotide inhibition strand, which is bonded to the particle surface, e.g. by covalent bonding using a bifunctional crosslinker such as sulfo-SMCC. The base sequences of the catalytic nucleic acid and the inhibitor strand are fully hybridized under physiological conditions, with this being achieved using a largely complementary to completely complementary base sequence.

In this case, the catalytically active nucleic acid and/or oligonucleotide inhibition strand are selected from the group of RNA, DNA, L-RNA, L-DNA, and modified nucleic acids. Examples of modified nucleic acids include nucleic acids that have lower nuclease sensitivity than the equivalent naturally-occurring nucleic acids. Examples of modified nucleic acids include LNA, PNA, morpholinos (Karkare and Bhatnagar, 2006), or GNA (Zhang and Chaput, 2010). Examples of L-ribozymes are described for example in Seelig et al. (2000), U.S. Pat. No. 2,003,219,422, and DE 10 2009 007929. As described above, moreover, using modified nucleic acids, functional groups may be introduced for binding to the oligonucleotide, with said groups preferably being terminally incorporated. Specifically, an SH-modified nucleotide is used. This is preferably introduced into a terminal, specifically the 5' end of the oligonucleotide, during synthesis. This can then be coupled, for example using one of the crosslinkers sulfo-SMCC or sulfo-GMBS, to an amino group of an aminosilane-modified nanoparticle.

Specifically, the present invention concerns an active substance release system in which Linker 1, via reaction of

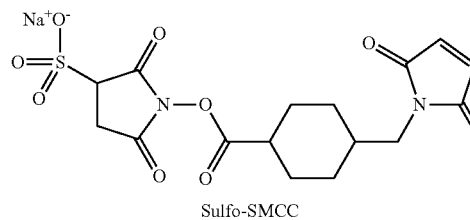

Sulfo-SMCC

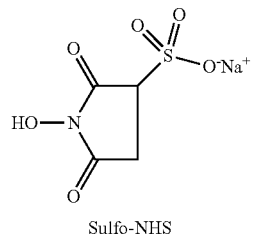

Sulfo-NHS

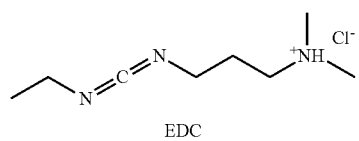

EDC

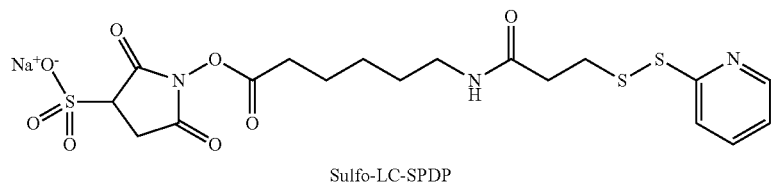

Sulfo-LC-SPDP an amino group with a crosslinker and the SH-group of the SH-modified nucleotide, is formed on the 5'-terminal of the oligonucleotide inhibitor strand, wherein the amino group was introduced onto the nanoparticle surface via aminosilane modification, and the crosslinker is preferably sulfo-SMCC or sulfo-GMBS.

The catalytically active nucleic acid preferably has a length of 10 to 100 nucleotides, and more preferably a length of 12 to 60 nucleotides. Suitable catalytic nucleic acids are known in the art. If necessary, these are further elongated at their 5'- or 3'-terminals in order to set a suitable hybridization temperature or incorporate modified nucleic acids.

RNA or DNA should preferably be used as the catalytically active nucleic acid. In nature, catalytically active nucleic acid molecules possess sequence specificity. This sequence specificity is attributable to specific base pairs formed near the cleavage site between the catalytic nucleic acids and the substrate oligonucleotide. Theoretically, catalytically active nucleic acids can be constructed in such a manner that any nucleotide sequence can be cleaved in a species-specific manner.

In addition to naturally occurring catalytic nucleic acids such as hammerhead, hairpin, ribonuclease P, and hepatitis delta virus ribozymes, a series of synthetic RNA molecules have been developed, and the catalytic activity thereof has increased dramatically in recent years as a result of development of in vitro selection techniques (Carmi et al., 1998). In this connection, "DNAzymes" are a recent product of biotechnological development. In this process, DNA molecules with catalytic activity are obtained exclusively by in vitro selection processes. They can cleave both DNA and RNA. An example of such a molecule having RNase activity is 10-23 DNAzyme (Santoro et al., 1997).

In a further embodiment, the present invention concerns an active substance release system wherein the catalytically active nucleic acid is selected from the group consisting of RNA, DNA, L-RNA, L-DNA, and a modified nucleic acid, the catalytically active nucleic acid preferably contains an SH-modified nucleotide, the catalytically active nucleic acid preferably has a length of 10 to 100 nucleotides, and more preferably a length of 12 to 60 nucleotides, and wherein the catalytically active nucleic acid is preferably RNA, specifically a ribozyme, specifically a hammerhead ribozyme, and specifically containing the sequence 5'-GGC UCG ACU GAU GAG GCG C-3' (SEQ ID NO: 1).

The catalytic nucleic acids according to the invention include hammerhead, hairpin, ribonuclease P, and hepatitis delta virus ribozymes, as well as ribozyme analogs derived therefrom and additional synthetic ribozymes and "DNAzymes." In this case, hammerhead enzymes are a particularly preferred embodiment of the present invention.

Naturally occurring hammerhead ribozymes, e.g. from plant viruses, typically consist of an individual auto-cleaving RNA molecule. In this case, the sequence consists of a minimum of three double helices that are bonded to one another by short linkers of preserved sequences. The preserved uridine turn bonds Helix 1 to Helix 2. Helix 2 and Helix 3 are bonded to each other by the sequence GAAA. In addition, a hammerhead ribozyme contains at least one loop.

In a particularly preferred embodiment, the catalytically active nucleic acid is an L-RNA, L-DNA, and/or a modified nucleic acid. For example, modified nucleic acids are understood to be those having lower nuclease sensitivity. Modified nucleic acids can also be used in order to incorporate suitable coupling groups into the oligonucleotide.

Particularly preferred are ribozymes, specifically hammerhead ribozymes. A particularly preferred catalytic nucleic acid contains the sequence 5'-GGC UCG ACU GAU GAG GCG C-3' (SEQ ID NO: 1).

The oligonucleotide inhibition strand is constructed in a manner that corresponds to the catalytically active nucleic acid according to common technical knowledge in the art. Accordingly, the oligonucleotide inhibition strand of the active substance release systems is also RNA or DNA, specifically L-RNA, L-DNA, and/or modified nucleic acids that have lower nuclease sensitivity.

Corresponding to the active nucleic acid, the inhibitor strand preferably has a length of 10 to 100 nucleotides, more preferably a length of 10 to 60 nucleotides, and it specifically contains the sequence 5'-G CCT CAT CAG TCG AGC C-3' (SEQ ID NO: 2).

A nucleic acid having a length of 10 to 100 nucleotides, and preferably 10 to 60 nucleotides, is preferably used as the oligonucleotide inhibition strand. The selected length of >10 nucleotides is selected for the purpose of hybridization stability, and the length of <100 nucleotides specified because of the high cost of synthetic production of long oligonucleotides. As a rule, these nucleic acids are selected in such a way that they are completely hybridized under physiological conditions because of their base pairing with the catalytic nucleic acid and are therefore largely complementary to the catalytic nucleic acid. A particularly preferred nucleic acid contains the sequence 5'-G CCT CAT CAG TCG AGC C-3' (SEQ ID NO: 2).

In a preferred embodiment, therefore, the invention concerns an active substance release system in which the oligonucleotide inhibition strand is selected from the group consisting of RNA, DNA, L-RNA, L-DNA, and a modified nucleic acid, specifically containing a SH-modified nucleotide, preferably having a length of 10 to 100 nucleotides, specifically having a length of 10 to 60 nucleotides, and specifically containing the sequence 5'-G CCT CAT CAG TCG AGC C-3' (SEQ ID NO: 2).

The molar ratio of oligonucleotide inhibition strands to catalytically active nucleic acids is preferably ≥1, and specifically 1 to 2, in order to ensure complete hybridization of the catalytic nucleic acid. In the practical example with the oligonucleotide inhibition strand containing the sequence SEQ ID NO: 2 and the catalytically active nucleic acid containing the sequence SEQ ID NO: 1, in vitro experiments using gel electrophoresis showed an optimum ratio and sufficient stability at T<43° C. of 1.0 to 1.3, and specifically of approx. 1.1.

In a preferred embodiment, the present invention thus concerns an active substance release system wherein in Compound 1, the ratio of the oligonucleotide inhibition strands to the catalytically active nucleic acid is ≥1, and specifically 1 to 2.

In another preferred embodiment, the present invention concerns an active substance release system wherein in Compound 1, the ratio of the oligonucleotide inhibition strands having the sequence 5'-G CCT CAT CAG TCG AGC C-3' (SEQ ID NO: 2) to the catalytically active nucleic acid having the sequence 5'-GGC UCG ACU GAU GAG GCG C-3' (SEQ ID NO: 1) is 1.0 to 1.3, and specifically approx. 1.1.

In the active substance release system according to the invention, the catalytically active nucleic acid should be completely hybridized with the oligonucleotide inhibition strand under physiological conditions, specifically up to a body temperature of below 43° C. At temperatures of 43° C. and above, preferably at least 5%, more preferably 10%, and specifically 20% of the total content of the catalytically active nucleic acid will be dehybridized. The release of at least one catalytic nucleic acid can be measured in buffer in a release assay as discussed in Example 3. The significant release of the fluorescent dye indicates dehybridization of at least one catalytic nucleic acid. In this manner, one can ensure that the active substance is released from Compound 2 only at elevated temperatures, e.g. through heating of the nanoparticles in a magnetic field.

Specifically, the invention thus concerns an active substance release system in which the catalytically active nucleic acid is completely hybridized with the oligonucleotide strand under physiological conditions, and in which at 43° C., at least one catalytically active nucleic acid, preferably 5%, more preferably 10%, and specifically 20% of the bonded catalytically active nucleic acids are dehybridized.

The nanoparticle of Compound 1 preferably comprises a core that contains a para- or superparamagnetic iron oxide. Suitable nanoparticles are described in the prior art. Specifically, the nanoparticles described in WO 97/38058, WO 98/58673, and WO 2009/086824 (all incorporated herein by reference) are suitable for the system according to the invention.

In a further embodiment, the invention concerns an active substance release system in which the nanoparticle has a core containing at least one paramagnetic or superparamagnetic iron oxide.

These nanoparticles preferably consist of a magnetic material, preferably a ferromagnetic, antiferromagnetic, ferrimagnetic, antiferrimagnetic, or superparamagnetic material, and more preferably iron oxides, specifically superparamagnetic iron oxides or pure iron provided with an oxide layer. These iron-based materials are selected in particular for their low toxicity, but other metal oxides are also suitable as a rule. Preferred iron oxides are magnetite ($Fe_3O_4$), maghemite ($\gamma$-$Fe_2O_3$), or mixtures of these two oxides. Generally speaking, the preferred nanoparticle can be represented by the formula $FeO_X$, where X is the number 1 or 2.

In addition to the magnetic material formula $FeO_X$, where X is a number in the range of 1.0 to 2.0, materials having the general formula $MFe_2O_4$, in which M=Co, Ni, Mn, Zn, Cd, or Ba or other ferrites can also be used. Moreover, silica or polymer particles with intercalated and/or bonded magnetic materials such as the magnetic materials specified herein are also suitable.

A further preferred embodiment of the present invention concerns an active substance release system in which the paramagnetic or superparamagnetic nanoparticles are heated in an alternating magnetic field.

In general, in a preferred embodiment, the heat required for the present invention is produced by an extracorporeal alternating magnetic field that excites the preferably superparamagnetic nanoparticle, which chiefly causes hysteresis heat to be released. Suitable devices are described for example in WO 2001/10501, WO 2001/10500, and WO 2009/118091. An extracorporeally applied alternating magnetic field can be internally strengthened (WO 2009/118091). As an alternative, the alternating magnetic field can also be internally induced (WO 2009/118091). This heat release produces the elevated temperature required in order to release the catalytically active nucleic acid.

In order to heat the paramagnetic or superparamagnetic nanoparticles in the alternating magnetic field, particular frequencies in the range of 10-500 kHz and field intensities of 0.5-50 kA/m, specifically 50-200 kHz and field intensities of 0.5-20 kA/m, are used. These ranges are particularly well tolerated in the treatment of humans, and have already been clinically tested. It is possible to heat the tissue containing the nanoparticles to over 80° C., and specifically to temperatures of between 43° C. and 55° C., independently of the specific absorption rate of the particles and their concentration in the target tissue.

The production of nanoparticles, but without an active substance or a coating, is extensively described in U.S. Pat. No. 6,048,515. As functionalization of the surface of the nanoparticles is known in the art, a known process can be used to produce hydroxy groups, carboxyl groups, thiol groups, epoxide groups, or carbonyl groups on the surface of the nanoparticles.

The nanoparticles are preferably based on magnetic ferrous cores enclosed in one or more colloidal coverings or coatings. In this case, the core preferably consists of magnetite or maghemite. The primary function of the coverings is to achieve a colloidal dispersion in an aqueous medium and protect the nanoparticles from agglomerations. Particles covered with multiple layers, such as those described in WO 98/58673, are as a rule suitable as a base for the nanoparticle conjugates, as the biological behavior of such particles can be adjusted by means of polymer coatings.

In the active substance release system according to the invention of the examples, an iron oxide core with a diameter of 15 nm (TEM) that was provided with a reactive silane covering, and more precisely an aminosilane covering, was selected.

In order to improve the coupling efficacy on the surface and reduce the activity of the iron oxide surface, the nanoparticles according to the present invention of Compound 1 should contain at least one covering, preferably a silane covering or an $SiO_2$-covering and a silane covering. These particles are superparamagnetic and have the advantage over pure iron particles of an inert surface. This protects the iron oxide core from reactions in the physiological medium; the $SiO_2$ surface is also advantageous in that its functional density is increased compared to pure iron oxide by condensation of the reactive silane on the available SiOH. It is preferred to coat the nanoparticles with an $SiO_2$-layer measuring 1-20 nm, and specifically 5 nm in thickness before applying the functional silane covering.

Specifically, the present invention concerns an active substance release system in which the nanoparticle has at least one covering, preferably a silane covering or an $SiO_2$ and silane covering.

However, it is also possible to use nanoparticles made of a non-magnetic material such as silicon dioxide ($SiO_2$) (see below) or gold (Au). If nanoparticles made of non-magnetic materials are used, stimulation and heat production are carried out in the range of the nanoparticles, not with an alternating magnetic field, but e.g. with infrared irradiation.

The nanoparticles should have a diameter of less than 500 nm. Preferably, the nanoparticles have an average diameter of 15 nm or are within the size range of 1-100 nm, and more preferably in the range of 10-20 nm.

The substrate molecule must be cleavable by the catalytically active nucleic acid so that the active substance can be released from the carrier substrate molecule-active substance conjugate and exert its action. As a rule, the substrate molecule is an oligonucleotide, but it can also be a cleavable peptide or another molecule suitable for the catalytically active nucleic acid.

Specifically, the present invention concerns an active substance release system in which the substrate molecule is an oligonucleotide.

The carrier of Compound 2 can be a polymer (e.g. a polylactide glycolide), specifically a biopolymer, an $SiO_2$ particle, or a metallic particle such as a gold particle or oxide particle. Suitable biopolymers include sugar, dextrans, chitosans, or starch. A small surface-modified iron oxide particle is also preferred in this case. The carrier may be in the form of a gel, microparticles, microspheres, or nanoparticles. According to a particularly preferred embodiment, Compound 2 is also in the form of a small surface-modified oxide particle, as described above for Compound 1. In this case, it can even be the same nanoparticle as that of Compound 1. Nanoparticle-containing medical products such as those described in WO 2009/100716 are also preferred (incorporated herein by reference). In one embodiment, the oligonucleotide inhibition strand, hybridized with the catalytically active nucleic acid, and the substrate molecule-active substance conjugate can be bonded to the same nanoparticle.

A further preferred embodiment of the present invention thus concerns an active substance release system in which the carrier is a polymer, specifically a biopolymer, an $SiO_2$ particle, or a metallic particle, specifically a gold particle, or an oxide particle, preferably a small surface-modified iron oxide particle, which is present in the form of a gel, microparticles, microspheres, or nanoparticles, specifically as oxide nanoparticles.

The active substance release system according to the invention comprises two types of nanoparticles in one embodiment: on the one hand, nanoparticles that contain the active substance bonded via the substrate oligonucleotide and optionally a linker to the magnetic nanoparticle, and on the other hand, nanoparticles that contain the catalytically active nucleic acid hybridized with an oligonucleotide inhibition strand. One can also use a single-component system in which both parts (the catalytically active nucleic acid and the substrate) are bonded to a single particle.

Thus the present invention also concerns a nanoparticle that is bonded to an oligonucleotide inhibition strand, said strand being hybridized with a catalytically active nucleic acid that is capable of cleaving a substrate oligonucleotide, which is bonded to another nanoparticle and to a therapeutically active substance.

The present invention also concerns a nanoparticle that is bonded to a therapeutically active substance and a substrate oligonucleotide, wherein the substrate oligonucleotide is cleavable by a catalytically active nucleic acid.

The functional principle of the active substance release system according to the invention is as follows. The catalytically active nucleic acid is hybridized with an oligonucleotide inhibition strand and released only at elevated temperature, i.e. above 38° C., and preferably above 40°. This ensures that under physiological conditions and at temperatures of up to 38° C., no release of the catalytically active nucleic acid occurs.

The oligonucleotide inhibition strand hybridized with the catalytically active nucleic acid is in turn bonded to a magnetic nanoparticle, and preferably to a superparamagnetic nanoparticle.

The active substance to be released, which is preferably an anticancer agent, is bonded via a substrate oligonucleotide, and optionally a linker, to another nanoparticle, but can also be bonded to the same nanoparticle as the oligonucleotide inhibition strand with the hybridized catalytically active nucleic acid.

Carrier- and/or particle-active substance conjugates also offer the advantage of concentrating in tumor cells or bacterial cells, and when e.g. MRT (magnetic resonance tomography) is used, they can detect not only tumors of small size, but even individual tumor cells. For example, this highly-sensitive detection method makes it possible to determine the occurrence and size of metastases. The nanoparticles according to the invention and the active substance release system according to the invention can be used in this detection method.

The active substance is so strongly, and preferably covalently, bonded to the substrate oligonucleotide that essentially no cleavage of the active substance occurs under physiological conditions. The nanoparticle to which the substrate oligonucleotide is optionally bonded via a linker is also preferably a magnetic particle, and more specifically a superparamagnetic particle in the nm to µm size range.

Thus it is possible, by applying a specific external alternating magnetic field, to increase the temperature in the range of the nanoparticle to such an extent that the hybridized catalytically active nucleic acid is released. The catalytically active nucleic acid then bonds to the substrate oligonucleotide and cleaves it, releasing the active substance from the nanoparticle and allowing it to exert its effect.

The increase in efficacy compared to the process described in WO2006/108405 occurs due to largely quantitative cleavage and release of the active substance, because the heat produced means that it is not the active substance itself that must be released, which as a rule does not occur quantitatively with small temperature changes, but only catalytic amounts of the catalytically active nucleic acid, and these do not have to be quantitatively released because catalytic amounts alone are sufficient to cleave the substrate oligonucleotide. Thus a catalyst is released in a non-quantitative manner, with said catalyst being capable of quantitatively releasing the active substance. This results in an increase in efficacy of almost 100% compared to the process according to WO2006/108405, in which the active substance is directly released as a result of the heat produced.

Figure 2:
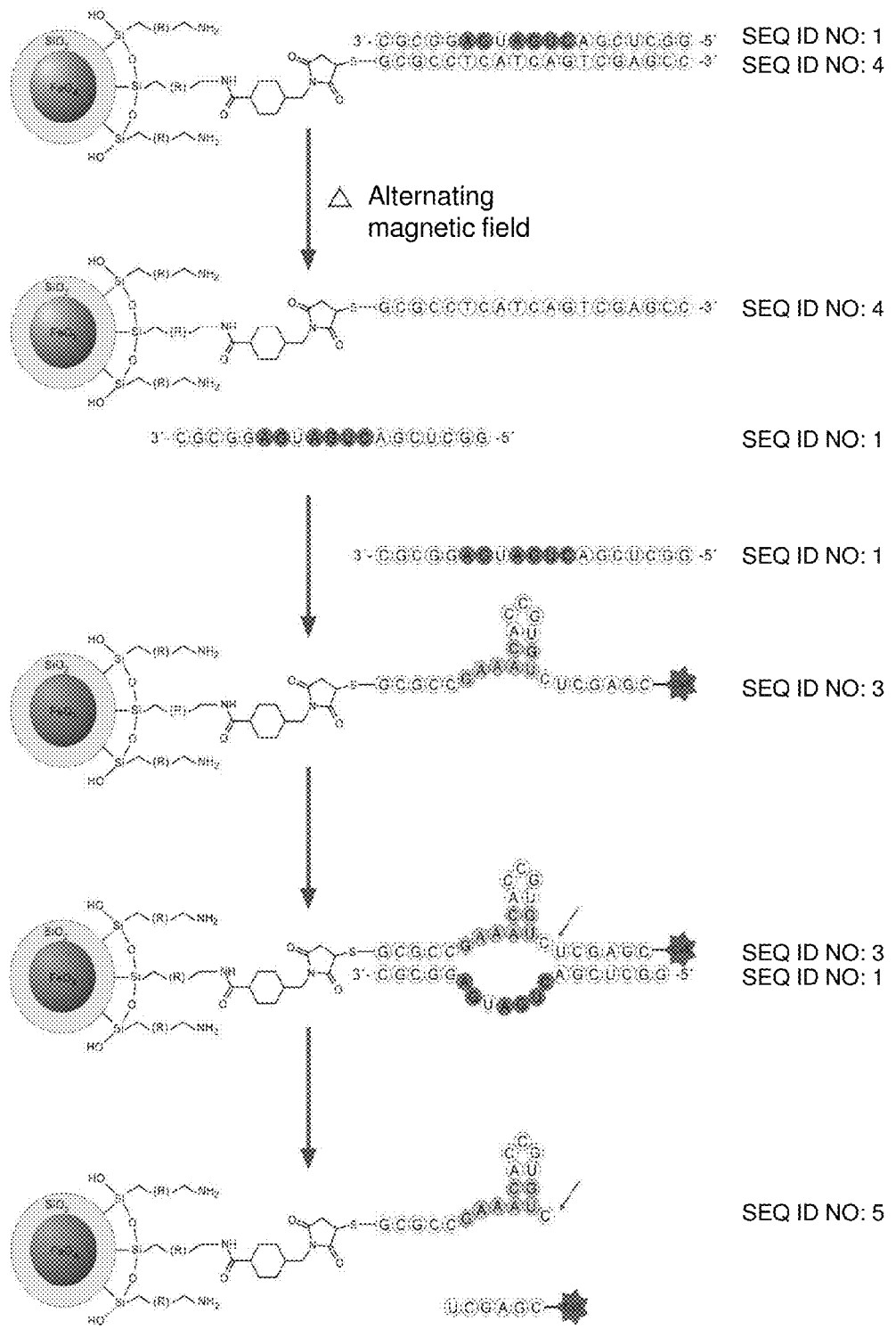

FIG. 2 shows a working example of the active substance release system according to the invention.

The nanoparticle-active substance conjugates are composed of nanoparticles (e.g. iron oxide, gold, $SiO_2$, or core-shell particles made of various, preferably superparamagnetic, materials), optional crosslinkers, and substrate oligonucleotides (DNA, RNA, modified nucleic acids, and nucleic acid analogs), which carry an active substance and can be specifically cleaved by corresponding catalytic nucleic acids. The catalytic nucleic acids from the first component serve after thermal release as cutting tools for cleaving the substrate oligonucleotide strand. The active substance, symbolized by the star in FIG. 2, is then released.

The advantage of the active substance release system according to the invention lies in the catalytic activity of the nucleic acids and the resulting increased efficacy in enzymatic release of the active substance from the nanoparticle-active substance conjugate. Because of the enzymatic nature of the catalytically active nucleic acids, only low concentrations of said catalytic nucleic acids are required to release a therapeutically effective concentration of the active substance from the nanoparticle-active substance conjugate.

The problem of less-than-optimal efficacy in thermal release of the active substance is thus solved in that the active substance in the nanoparticle-active substance conjugate is released enzymatically rather than thermally. In this manner, the thermal release of very small amounts of catalytic nucleic acids is sufficient to achieve the enzymatic release of large amounts of the active substance in tumor cells.

Further advantages of the active substance release system lie in its great variability and adaptability to various situations. The temperature-dependent activation of the catalytic nucleic acids can be modified as desired, e.g. by means of the length of the inhibitor sequence or the hybridization ratios between the inhibitor and the catalytic nucleic acids. The rate of active substance release and/or the amount of the active substance released are dependent on the local temperature and/or the concentrations of the components, so possible side effects of the active substance on normal cells can be selectively minimized.

In the active substance release system according to the invention, the substrate molecule is covalently bonded, and preferably via Linker 2, to the carrier. Linker 2 is selected according to common knowledge in the art based on the available reactive groups of the carrier and/or the substrate molecules. If necessary, a modified nucleic acid, specifically a terminally modified nucleic acid, is used for example to make an amino group available on the substrate oligonucleotide side. As a rule, the same crosslinkers as those described above for Linker 1 can be used. Preferred linkers are sulfo-SMCC and sulfo-GMBS.

In another preferred embodiment, the present invention concerns an active substance release system in which the substrate molecule is bonded covalently, specifically covalently via Linker 2, to the carrier, and in which the linker is preferably sulfo-SMCC or sulfo-GMBS.

The substrate oligonucleotide is preferably selected from the group consisting of DNA, RNA, L-DNA, L-RNA, and modified nucleic acids. Modified nucleic acids are preferably those having low nuclease sensitivity, in order to inhibit and/or prevent spontaneous release due to the activity of the naturally occurring nucleases. In addition, modified nucleotides can be incorporated that have an additional reactive group, namely a functional group for coupling. These groups are preferably terminally incorporated. Specific preferred functional groups include amino, thiol, carboxyl, alkyne, or azide functional groups.

Specifically, the present invention thus concerns an active substance release system in which the substrate oligonucleotide is selected from the group consisting of DNA, RNA, L-DNA, L-RNA, and a modified nucleic acid, wherein the modified nucleic acid preferably has a terminal functional group, specifically an amino, thiol, carboxyl, alkyne, or azide functional group.

As a rule, any molecule that can be cleaved by the catalytically active nucleic acids selected for Compound 1 can be used as a substrate molecule. This cleavage should preferably be specific. Corresponding pairs of catalytic nucleic acids and their substrates are sufficiently well-known in the prior art. Substrate oligonucleotides preferably have a length of 10 to 100 nt, more preferably 15-60 nt, and specifically 20-30 nt. On the other hand, oligonucleotides larger than 100 nt are generally too expensive. Recognition sequences of substrates are at least 10 nt long as a rule. In accordance with the catalytically active nucleic acid used in the examples, a substrate oligonucleotide containing the sequence 5'-GCG CCG AAA CAC CGU GUC UCG AGC-3' (SEQ ID NO: 3) is preferred.

Thus a further embodiment of the present invention concerns an active substance release system in which the substrate oligonucleotide has a length of 10 to 100 nucleotides, preferably a length of 15 to 60 nucleotides, even more preferably a length of 20 to 30 nucleotides, and specifically contains the sequence 5'-GCG CCG AAA CAC CGU GUC UCG AGC-3' (SEQ ID NO: 3).

The active substance release system according to the invention contains at least one therapeutically active substance that is selected from the group comprising nucleic acids, siRNAs, antisense RNAs, amino acids, aptamers, peptides, proteins, glycoproteins, carbohydrates, glycans, lipids, lipoproteins, and low-molecular-weight active substances. Low-molecular-weight active substances are particularly preferred.

These are preferably antiproliferative, cytostatic, cytotoxic, antimigrative, antiangiogenic, antithrombotic, anti-inflammatory, antiphlogistic, anticoagulant, antibacterial, antiviral and/or antimycotic active substances, particularly substances having a cytostatic or cytotoxic action, with antiproliferative, antimigrative, anti-angiogenic, cytostatic and/or cytotoxic active substances, as well as nucleic acids, specifically including inhibitory nucleic acids (e.g. siRNA), amino acids, peptides, proteins, carbohydrates, lipids, glycoproteins, glycans or lipoproteins having antiproliferative, antimigrative, anti-angiogenic, antithrombotic, anti-inflammatory, antiphlogistic, cytostatic, cytotoxic, anticoagulant, antibacterial, antiviral and/or antimycotic properties being preferred. In addition, these substances can also be radiosensitizers, sensitizers, or enhancers of other conventional cancer treatment methods, including combined treatment, or they may contain such sensitizers.

Specifically, the present invention thus concerns an active substance release system in which the therapeutically active substance is selected from the group comprising nucleic acids, siRNAs, antisense RNAs, amino acids, aptamers, peptides, proteins, glycoproteins, carbohydrates, glycans, lipids, lipoproteins, and low-molecular-weight active substances, with said therapeutically active substance specifically being a low-molecular-weight active substance, and preferably a substance having an antiproliferative, cytostatic, cytotoxic, antimigrative, anti-angiogenic, antithrombotic, anti-inflammatory, anti-phlogistic, anticoagulant, antibacterial, antiviral and/or antimycotic action, particularly a cytostatic or cytotoxic action, with the therapeutically active substances doxorubicin or methotrexate being preferred.

Substances that can be used as cytotoxic and/or cytostatic compounds, i.e. chemical compounds with cytotoxic and/or cytostatic properties, include alkylating agents, antibiotics with cytostatic properties, antimetabolites, microtubule inhibitors and topoisomerase inhibitors, platinum-containing compounds, and other cytostatics such as asparaginase, tretinoin, alkaloids, podophyllotoxin, taxane and Miltefosine®, hormones, immunomodulators, monoclonal antibodies, signal transducers (signal transduction molecules), and cytokines.

Examples of alkylating agents include chlorethamine, cyclophosphamide, trofosfamide, ifosfamide, melphalan, chlorambucil, busulfan, thiotepa, carmustine, lomustine, dacarbazine, procarbazine, temozolomide, treosulfan, estramustine, and nimustine.

Antibiotics with cytostatic properties include daunorubicin, as well as liposomal daunorubicin, doxorubicin (Adriamycin), dactinomycin, mitomycin C, bleomycin, epirubicin (4-Epi-Adriamycin), idarubicin, dactinomycin, mitoxantrone, amsacrine, and actinomycin D.

Methotrexate, 5-fluorouracil, 6-thioguanine, 6-mercaptopurine, fludarabine, cladribine, pentostatin, gemcitabine, cytarabine, azathioprine, raltitrexed, capecitabine, cytosine arabinoside, thioguanine, and mercaptopurine can be mentioned as examples of antimetabolites (antimetabolic active substances).

Examples of the class of the alkaloids and podophyllotoxins include vincristine, vinblastine, vindesine, etoposide, and teniposide. In addition, platinum-containing compounds may be used in the invention. Examples of platinum-containing compounds include cisplatin, carboplatin, and oxaliplatin. Examples of the microtubule inhibitors include alkaloids such as vinca-alkaloids (vincristine, vinblastine, vindesine, vinorelbine) and paclitaxel (Taxol®), as well as derivatives of paclitaxel. Examples of topoisomerase inhibitors include etoposide, teniposide, camptothecin, topotecan, and irinotecan.

Paclitaxel and docetaxel are examples of the compound class of the taxanes, and examples of other cytostaticically active substances (other cytostatics) include hydroxycarbamide (hydroxyurea), imatinib, Miltefosine®, amsacrine, topotecan (a topoisomerase-1-inhibitor), pentostatin, bexarotene, tretinoin, and asparaginase. Representatives of the compound class of monoclonal antibodies include trastuzumab (Herceptin®), alemtuzumab (MabCampath®), and rituximab (MabThera®).

Hormones such as glucocorticoids (prednisone), estrogens (fosfestrol, estramustine), LHRH (buserelin, goserelin, leuprorelin, triptorelin), flutamide, cyproterone acetate, tamoxifen, toremifene, aminoglutethimide, formestane, exemestane, letrozole, and anastrozole may also be used. Examples of compounds from the classes of the immunomodulators, cytokines, antibodies, and signal transducers include interleukin-2, interferon-α, erythropoietin, G-CSF, trastuzumab, rituximab, efitinib (Iressa®), ibritumomab (Zevalin®), levamisole, and retinoids.

The active substance to be released may also be an opioid agonist, a non-opioid analgesic, a nonsteroidal anti-inflammatory (NSAID) active substance, an anti-migraine active substance, a cox-II inhibitor, a β-adrenergic blocker, an anticonvulsant, an antidepressant, a $Ca^{2+}$ channel blocker, or an active substance for the treatment of neuronal or neurodegenerative diseases such as Parkinson's disease, anxiety, epilepsy, stroke, psychoses, cognitive disorders, or depression.

The active substance release system according to the invention and pharmaceutical compounds are used for both treatment and prevention of diseases in which the properties of controlled active substance release can be taken advantage of in order to release the active substance in a controlled manner, in therapeutically relevant concentrations, and in the cells of the target tissue.

A further significant advantage of the present invention is the possibility of controlled time-dependent release of an active substance bonded to the particles, on the one hand by applying an external alternating magnetic field in the case of magnetic particles, or by irradiation with infrared light in the case of non-magnetic particles. This makes it possible to release the active substance in a targeted and time-controlled manner at a specific time, for example during a migraine attack or on occurrence of severe pain, in order to treat disorders, pain, or other diseases.

As a result, the active substance release system and the pharmaceutical compounds contained therein are also for the prevention and treatment of pain, neurodegenerative diseases, and cardiovascular diseases.

The following are examples of useful opioid agonists: alfentanil, allylprodine, alphaprodine, anileridine, benzylmorphine, bezitramide, buprenorphine, butorphanol, clonitazene, codeine, desomorphine, dextromoramide, dezocine, diampromide, diamorphine, dihydrocodeine, dihydromorphine, dimenoxadol, dimepheptanol, dimethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papavereturn, pentazocine, phenadoxone, phenomorphan, phenazocine, phenoperidine, piminodine, piritramide, proheptazine, promedol, properidine, propiram, propoxyphene, sufentanil, tilidine, tramadol, and pharmaceutically acceptable salts and mixtures thereof.

The following are examples of useful non-opioid analgesics, including nonsteroidal anti-inflammatory (NSAID) active substances: aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenaminic acid, meclofenaminic acid, flufenaminic acid, niflumic acid, tolfenaminic acid, diflurisal, flufenisal, piroxicam, sudoxicam, isoxicam and pharmaceutically acceptable salts and mixtures thereof.

Further non-opioid analgesics comprise the following chemical classes of analgesics, antipyretics, and nonsteroidal anti-inflammatory (NSAID) active substances: salicylic acid derivatives, including aspirin, sodium salicylate, choline-magnesium-trisalicylate, salsalate, diflunisal, salicyl salicyclic acid, sulfasalazine and olsalazine; para-aminophenol derivatives, including acetaminophen and phenacetin; indol- and indenacetic acid, including indomethacin, sulindac and etodolac; heteroarylacetic acids, including tolmetin, diclofenac and ketorolac; anthranilic acids (fenamate), including mefenaminic acid and meclofenaminic acid; enolic acids, including oxicams (piroxicam, tenoxicam) and pyrazolidinedione (phenylbutazone, oxyphenthartazone); and alkanones, including nabumetone.

The following are examples of useful cox-ii inhibitors and 5-lipoxygenase inhibitors: celecoxib, etoricoxib, rofecoxib, parecoxib, and valdecoxib.

The following are examples of useful anti-migraine active substances: alpiropride, bromocriptine, dihydroergotamine, dolasetron, ergocornine, ergocornine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan and mixtures thereof.

The following are examples of useful β-adrenergic blockers: acebutolol, alprenolol, amosulalol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, chloranolol, dilevalol, epanolol, esmolol, indenolol, labetalol, levobunolol, mepindolol, metipranolol, metoprolol, moprolol, nadolol, nadoxolol, nebivolol, nifenalol, nipradilol, oxprenolol, penbutolol, pindolol, practolol, pronethalol, propranolol, sotalol, sulfinalol, talinolol, tertatolol, tilisolol, timolol, toliprolol, and xibenolol.

The following are examples of useful anticonvulsants: acetyl pheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluorexon, gabapentin, 5-hydroxytryptophan, lamotrigine, magnesium bromide, magnesium sulfate, mephenyloin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenyloin, phethenylate sodium, potassium bromide, pregabalin, primidone, progabide, sodium bromide, solanum, strontium bromide, suclofenide, sulthiame, tetrantoin, tiagabine, topiramate, trimethadione, valproic acid, valpromide, vigabatrin, and zonisamide.

The following are examples of useful antidepressants: binedaline, caroxazone, citalopram, (s)-citalopram, dimethazan, fencamine, indalpine, indeloxazine hydrochloride, nefopam, nomifensine, oxitriptan, oxypertine, paroxetine, setraline, thiazesim, trazodone, benmoxin, iproclozide, iproniazid, isocarboxazid, nialamide, octamoxin, phenelzine, cotinine, rolicyprine, rolipram, maprotiline, metralindole, mianserin, mirtazapine, adinazolam, amitriptyline, amitriptyline oxide, amoxapine, butriptyline, clomipramine, demexiptiline, desipramine, dibenzepin, dimetacrine, dothiepin, doxepin, fluacizine, imipramine, imipramine n-oxide, iprindole, lofepramine, melitracen, metapramine, nortriptyline, noxiptiline, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, I-tryptophan, venlafaxine, viloxazine, and zimelidine.

The following are examples of useful $Ca^{2+}$-channel blockers: bepridil, clentiazem, diltiazem, fendiline, gallopamil, mibefradil, prenylamine, semotiadil, terdilin, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone and perhexyline.

The following are examples of useful active substances for the treatment of neuronal or neurodegenerative diseases such as Parkinson's disease, anxiety, epilepsy, stroke, psychoses, cognitive disorders, or cognitive disorders, or depression: L-dopa, anticholinergics, COMT inhibitors, serotonin reuptake inhibitors, buspirone, tricyclic antidepressants, monoaminoxidase inhibitors, valproic acid, carbamazepine, selective serotonin reuptake inhibitors, serotonin-noradrenaline reuptake inhibitors, noradrenaline-serotonin-selective antidepressants and trimipramine.

For the treatment or prevention of Parkinson's disease: carbidopa/levodopa, pergolide, bromocriptine, ropinirole, pramipexole, entacapone, tolcapone, selegiline, amantadine, and trihexyphenidyl-hydrochloride.

For the treatment or prevention of anxiety: benzodiazepines such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam and triazolam; non-benzodiazepine active substances such as buspirone, gepirone, ipsapirone, tiospirone, zolpicone, zolpidem and zaleplon; sedatives from the is barbiturate group such as amobarbital, aprobarbital, butabarbital, butalbital, mephobarbital, methohexital, pentobarbital, phenobarbital, secobarbital and thiopental; and propanediol carbamate, such as meprobamate, and tybamate.

For the treatment or prevention of epilepsy: carbamazepine, ethosuximide, gabapentin, lamotrigine, phenobarbital, phenyloin, primidone, valproic acid, trimethadione, benzodiazepine, γ-vinyl GABA, acetazolamide, and felbamate.

For the treatment or prevention of stroke: anticoagulant active substances, such as heparin, as well as active substances that can dissolve blood clots, such as streptokinase or tissue-specific plasminogen activators and active substances that reduce swelling, such as mannitol, corticosteroids or acetylsalicylic acid.

For the treatment or prevention of psychoses: phenothiazine, such as chlorpromazine hydrochloride, mesoridazine besilate and thioridazine hydrochloride; thioxanthene, such as chlorprothixene and thiothixene hydrochloride, clozapine, risperidone, olanzapine, quetiapine, quetiapine fumarate, haloperidol, haloperidol decanoate, loxapine succinate, molindone hydrochloride, primozide, and ziprasidone.

For the treatment or prevention of cognitive disorders: active substances for the treatment of dementia, such as tacrine; donepezil, ibuprofen and antipsychotic active substances such as thioridazine and haloperidol.

For the treatment or prevention of depression: amitriptyline, amoxapine, bupropion, clomipramine, desipramine, doxepin, imipramine, maprotiline, nefazodone, nortriptyline, protriptyline, trazodone, trimipramine, venlafaxine, citalopram, (s)-citalopram, fluoxetine, fluvoxamine, paroxetine, sertraline, isocarboxazid, pargyline, phenelzine, tranylcypromine, dextroamphetamine, and methylphenidate.

The aforementioned active substances are preferably covalently bonded to the substrate oligonucleotide. Bonding of the active substances can occur e.g. via hydroxy groups, amino groups, carbonyl groups, thiol groups or carboxyl groups, depending on the functional groups carried by the respective active substance.

Hydroxy groups are preferably bonded as esters, acetals, or ketals, thio groups preferably as thioesters, thioacetals, or thioketals, amino groups preferably as amides and in some cases also as imines (Schiff bases), carboxyl groups preferably as esters or amides, and carbonyl groups preferably as ketals.

According to one embodiment, the active substances doxorubicin and methotrexate are particularly preferred. Methotrexate can be covalently bonded via a methotrexate carboxy group by means of a peptide bond via an amino group that was preferably terminally incorporated into the substrate oligonucleotide. Doxorubicin could be coupled, for example as a prodrug, via a linker and the amino functional group, as is described in the prior art for albumin-doxorubicin conjugates (Abu Ajaj et al., 2009, Boga et al., 2009, Calderon et al., 2009, Kratz et al., 2008).

Bonding of at least one therapeutically active substance to the substrate oligonucleotide, i.e. bonding of the molecules of at least one therapeutically active substance class or a particular active substance, preferably takes place covalently or by primarily covalent bonding and/or by sufficiently strong ionic bonding, intercalative bonding, complex bonding or intercalation, so that uncontrolled release of the therapeutically active substance is largely eliminated. Uncontrolled release refers to the release of the therapeutically active substance in healthy tissue, specifically the detachment of the substrate oligonucleotide without cleavage by the catalytic nucleic acid of the first component.

Such uncontrolled release causes therapeutically active substances to be released at sites where they cause harmful side effects rather than therapeutic effects, e.g. outside of the carcinogenic tissue and/or the tumor cells.

In the first step, the catalytic nucleic acid is separated from its oligonucleotide inhibition strand, e.g. by means of an alternating magnetic field, specifically an external or externally applied alternating (pulsed) magnetic field or by IR irradiation with respect to gold nanoparticles. The free catalytic nucleic acid then bonds to the substrate oligonucleotide in the nanoparticle-active substance conjugate and releases the active substance together with the attached oligonucleotide via cleavage of the substrate. The single-stranded oligonucleotide is rapidly decomposed inside the cell, completely releasing the active substance.

According to one embodiment of the active substance release system, the therapeutically active substance is covalently bonded to the substrate oligonucleotide, specifically via Linker 3. This can take place as described above for Linkers 1 and 2 by direct bonding, specifically the formation of a peptide bond between the active substance and substrate molecule, but also via a homo- or heterobifunctional crosslinker.

According to a preferred embodiment, the present invention thus concerns an active substance release system in which the therapeutically active substance is covalently bonded to the substrate molecule, specifically via Linker 3.

According to one embodiment of the active substance release system according to the invention, Linker 3 is a peptide bond or a hydrazone, with the latter substance having the advantage that it can be cleaved off, in the acidic environment of the lysosome and/or the tumor, from the substrate residue, i.e. the portion still present on the active substance after cleavage, thus allowing the original structure of the active substance to be restored. Methotrexate can be covalently bonded via a methotrexate carboxy group by means of a peptide bond via an amino group that was preferably terminally incorporated into the substrate oligonucleotide. Doxorubicin can be coupled as a prodrug via the amino group (Abu Ajaj et al., 2009, Boga et al., 2009, Calderon et al., 2009, Kratz et al., 2008).

In a further embodiment, the present invention concerns an active substance release system in which Linker 3 is selected from the group consisting of an amino group and hydrazone, specifically wherein methotrexate is bonded via a methotrexate carboxy group by means of a peptide bond between the amino group.

In one embodiment, the therapeutically active substance is inactive as long as it is bonded to the substrate molecule and/or Linker 3. With the release from the substrate oligonucleotide and/or Linker 3 by cleavage of the substrate molecules or after subsequent uptake by a cell, the active substance is then activated. In one embodiment, the cleaved off active substance may still contain a portion of the now cleaved substrate molecules, as well as Linker 3, and thus be deactivated. In this case, crosslinkers that can be cleaved in the cell or by specific enzymatic cleavage, or that are acid-labile, may be used, specifically hydrazone, with said crosslinkers being cleaved on entry into the lysosome, thus releasing the active substance.

Thus in a further embodiment, the present invention concerns an active substance release system in which the therapeutically active substance is inactive as long as it is bonded to the substrate molecule and/or Linker 3, and it is activated when the therapeutically active substance is released from the substrate molecule and/or when Linker 3 is released, or after subsequent intake into a cell.

A short nucleotide strand may remain on the active substance after cleavage, but this will be decomposed under physiological conditions and has no effect or no substantial effect on the efficacy of the active substance.

In the case of only weak bonding of the active substance to the substrate oligonucleotide, for example in the case of non-covalent, ionic, adsorptive, lipophilic and/or Van der Waals bonds and/or hydrogen bonds, a protective covering or barrier coating can prevent the release of the therapeutically active substance until the nanoparticles have reached their intended destination. Instead of this protective covering or barrier coating, or as an additional layer on said protective covering or barrier coating, an external layer having cell-specific functionality can be applied.

This cell-specific coating increases the affinity of the nanoparticles for certain cells, for example for certain bacterial cells or certain tumor cells, and is therefore useful for cell discrimination. Such cell-specific nanoparticles tend to concentrate in such cells, for which they have an increased affinity because of their surface functionality, and they are thus tumor-specific. With this technology, for example, tumor-specific nanoparticles can be developed for certain kinds of cancer.

Moreover, the nanoparticles can also be stabilized by colloidal protective coverings, which protect the nanoparticles from an agglomeration. Such protective coverings or coatings should preferably contain amino groups or carboxy groups. Biological, synthetic, or semisynthetic polymers can be used for the protective coverings and/or coatings. For producing a barrier coating, biostable polymers, i.e. those largely resistant to biological breakdown, should preferably be used. For the production of cell-specific coverings and/or coatings, biodegradable polymers should preferably be used.

The following can be used as biostable polymers: polyacrylic acid and polyacrylates such as polymethyl methacrylate, polybutyl methacrylate, polyacrylamide, polyacrylonitrile, polyamide, polyether amide, polyethylene amine, polyimide, polycarbonate, polycarbourethane, polyvinyl ketone, polyvinyl halogenide, polyvinylidene halogenide, polyvinyl ether, polyisobutylene, polyvinyl aromatic compounds, polyvinyl ester, polyvinyl pyrrolidone, polyoxymethylene, polytetramethylene oxide, polyethylene, polypropylene, polytetrafluoroethylene, polyurethane, polyether urethane silicone-polyether urethane, silicon-polyurethane, silicone-polycarbonate-urethane, polyolefin-elastomers, polyisobutylene, EPDM-rubbers, fluorosilicone, carboxymethyl chitosan, polyaryl ether ether ketone, polyether ether ketone, polyethylene terephthalate, polyvalerate, carboxymethylcellulose, cellulose, rayon, rayon triacetate, cellulose nitrate, cellulose acetate, hydroxyethyl cellulose, cellulose butyrate, cellulose acetate butyrate, ethylvinyl acetate copolymers, polysulfones, epoxy resins, ABS resins, EPDM rubbers, silicones such as polysiloxane, polydimethylsiloxane, polyvinyl halogens and copolymers, cellulose ether, and cellulose triacetate. Chitosans and copolymers and/or mixtures of these substances.

The following can be used as biodegradable polymers: polyvalerolactone, poly-ε-decalactone, polylactonic acid, polyglycolic acid, polylactide, polyglycolide, copolymers of polylactide and polyglycolide, poly-ε-caprolactone, polyhydroxybutyric acid, polyhydroxybutyrate, polyhydroxyvalerate, polyhydroxy-butyrate covalerate, poly(1,4-dioxane-2,3-dione), poly(1,3-dioxan-2-one), poly-paradioxanone, polyanhydrides such as polymaleic acid anhydride, polyhydroxymethacrylate, fibrin, polycyanoacrylate, polycaprolactone dimethyl acrylate, poly-β-maleic acid, polycaprolactone butyl acrylate, multiblock polymers such as polymers of oligocaprolactone diol and oligodioxanone diol, polyether ester multiblock polymers such as PEG and poly(butylene terephthalate), polypivotolactone, polyglycolic acid trimethyl carbonate, polycaprolactone glycolide, poly(-ethyl glutamate), poly(DTH-imino carbonate), poly(DTE-co-DT-carbonate), poly(bisphenol A-imino carbonate), polyorthoester, polyglycolic acid trimethyl carbonate, polytrimethyl carbonate, polyiminocarbonate, poly(N-vinyl)-pyrrolidone, polyvinyl alcohols, polyester amide, glycosylated polyester, polyphosphoester, polyphosphazene, poly[(p-carboxyphenoxy)propane]polyhydroxypentanoic acid, polyanhydride, polyethylene oxide, propylene oxide, soft polyurethane, polyurethane with amino acid residues in the backbone, polyether esters such as polyethylene oxide, polyalkene oxalate, polyorthoester, and their copolymers, lipids, carrageenans, fibrinogen, starch, collagen, protein-based polymers, polyamino acids, synthetic polyamino acids, zein, modified zein, polyhydroxyalkanoate, pectic acid, acetic acid, modified and unmodified fibrin and casein, carboxymethyl sulfate, albumin, hyaluronic acid, chitosan and its derivatives, heparan sulfate and its derivatives, heparins, chondroitin sulfate, dextran, β-cyclodextrins, alginates, glycosaminoglycans, saccharides, polysaccharides, proteoglycans, glycoproteins, copolymers with PEG and polypropylene glycol, gum arabic, guar, gelatins, collagen, collagen-N-hydroxysuccinimides, lipids, phospholipids, modifications and copolymers and/or mixtures of the aforementioned substances.

In order to further increase affinity with respect to certain cells, monoclonal antibodies and/or aptamers can be coupled to the surface of the nanoparticles and/or to the outer layer or covering of the nanoparticles. The monoclonal antibodies and aptamers are of such a conformation that they recognize certain cells, such as tumor cells, for example, and further increase the cell discrimination capacity of the nanoparticles.

In the active substance release system according to the invention, provided that the catalytically active nucleic acid is dissociated from the oligonucleotide inhibition strand, the substrate molecule can be cleaved. In the cleavage reaction of the substrate molecules via the catalytically active nucleic acid, the concentration of the substrate molecules is $\geq K_M$, wherein $k_{cat}$ is preferably $\geq 0.05$/min, more preferably $\geq 0.5$/min, even more preferably $\geq 1$/min, and specifically $\geq 5$/min.

The ratio of Compound 1 to Compound 2 in this case is $\leq 2$, specifically $\leq 1$.

This is attributable to the competitive reaction of inhibition and substrate cleavage. From a therapeutic standpoint, the rate constants of substrate cleavage should be as high as possible, and this should preferably be accompanied by a small amount of catalytically active nucleic acid.

In a concrete embodiment of the active substance release system according to the invention, the oligonucleotide inhibition strand, the catalytically active nucleic acid, and the substrate oligonucleotide are all mirror-image nucleic acids. The oligonucleotide inhibition strand should preferably be an L-DNA, specifically containing the sequence 5'-G CCT CAT CAG TCG AGC C-3' (SEQ ID NO: 2), the catalytically active nucleic acid should be an L-RNA, specifically containing the sequence 5'-GGC UCG ACU GAU GAG GCG C-3' (SEQ ID NO: 1), and the substrate oligonucleotide should be an L-RNA, specifically containing the sequence 5'-GCG CCG AAA CAC CGU GUC UCG AGC-3' (SEQ ID NO: 3). Using this compound, it was possible to create a particularly suitable active substance release system according to the examples.

A further object of this invention is Compound 1 as defined in the framework of this invention.

Compound 1 could be sold as an individual product, for example for patients who have previously received an implant of Compound 2, e.g. during previous surgery. In such cases, the active substance coupled to such an implant could be cleaved off and thus activated at a later time by separate administration of Compound 1. In this connection, the compound can be administered into the implant (e.g. in the case of sponge-like polymers), toward the implant (into the afferent (blood) vessels or a nearby local region), or administered systemically (e.g. i.v.), specifically when Compound 1 concentrates in the target tissue by means of a targeting mechanism.

Accordingly, a further object of this invention is Compound 2 as defined in the framework of this invention.

As described above, these compounds can be implanted at certain sites in the body at an earlier time, for example during surgery, in order to later release the coupled active substance locally.

The present invention also concerns pharmaceutical compounds and/or medicines that contain the active substance release system according to the invention or one of Compounds 1 or 2 according to the invention, as well as the use of the active substance release system according to the invention to manufacture such pharmaceutical compounds. Specifically, these pharmaceutical compounds are infusion or injection solutions. Such solutions of the nanoparticles, for example in physiological saline, are suitable for interstitial and/or intratumoral administration.

Moreover, intraarterial or intravenous application provides a systemic therapeutic modality for the entire body for non-solid and/or metastatic tumor times. The pharmaceutical compounds and/or medicines are formulated for administration using the methods known to a person skilled in the art, i.e., suitable buffers and excipients should be added as needed.

In a further embodiment, the present invention concerns a medication containing an active substance release system as defined in the framework of the present invention.

The active substance release system and pharmaceutical compounds according to the invention are used for both treatment and prevention of diseases characterized by degenerated cell species or exogenous cells and diseases in which the properties of controlled active substance release can be taken advantage of in order to release the active substance in a controlled manner, in therapeutically relevant concentrations, and only in the cells of the target tissue. Degenerated cells are considered to include specific cancer cells and/or cells showing abnormal proliferation, as well as tissue showing stenosis or residual stenosis. Bacteria can be mentioned as a specific example of exogenous cells.

Accordingly, the active substance release system and pharmaceutical compounds or medicines containing it are used for the prevention and/or treatment of proliferative diseases, tumors, carcinomas, cancer, inflammatory diseases, specifically autoimmune diseases, and bacterial infections.

In a preferred embodiment, the invention concerns a medication containing an active substance release system for the treatment and/or prevention of proliferative diseases, cancer, inflammatory diseases, specifically autoimmune diseases, and bacterial infections.

Examples of cancer and tumor types in which the nanoparticles according to the invention can be used are as follows: adenocarcinoma, choroidal melanoma, acute leukemia, acoustic neuroma, ampullary carcinoma, anal carcinoma, astrocytoma, basalioma, pancreatic cancer, connective tissue tumors, bladder cancer, bronchial carcinoma, non-small-cell bronchial carcinoma, breast cancer, Burkitt's lymphoma, corpus carcinoma, CUP syndrome, bowel cancer, small intestine cancer, small intestine tumors, ovarian cancer, endometrial carcinoma, ependymoma, epithelial cancers, Ewing tumors, gastrointestinal tumors, gallbladder cancer, cholangiocarcinoma, uterine cancer, cervical cancer, glioblastoma, gynecological tumors, ear, nose, and throat tumors, hematologic neoplasias, hairy cell leukemia, urethral cancer, skin cancer, brain tumors (glioma), brain metastases, testicular cancer, pituitary tumor, carcinoids, Kaposi's sarcoma, laryngeal cancer, germ cell tumor, bone cancer, colorectal carcinoma, head and neck tumors (tumors of the ear, nose, and throat region), colon carcinoma, craniopharyngioma, cancer of the oral area and lips, liver cancer, liver metastases, leukemia, eyelid tumor, lung cancer, lymph node cancer (Hodgkin's/non-Hodgkin's), lymphoma, stomach cancer, malignant melanoma, malignant neoplasia, malignoma of the gastrointestinal tract, breast carcinoma, rectal cancer, medulloblastoma, melanoma, meningioma, Hodgkin's disease, mycosis fungoides, nasal cancer, neurinoma, neuroblastoma, renal cancer, renal cell carcinomas, non-Hodgkin's lymphoma, oligodendroglioma, esophageal carcinoma, osteolytic carcinomas and osteoplastic carcinomas, osteosarcoma, ovarian carcinoma, pancreatic carcinoma, penis cancer, plasmocytoma, squamous epithelial carcinomas of the head and neck, prostate cancer, throat cancer, rectal carcinoma, retinoblastoma, vaginal cancer, thyroid carcinoma, Schneeberger's disease, esophageal cancer, spinalioma, t-cell lymphoma (mycosis fungoides), thymoma, tubal carcinoma, ophthalmic tumors, urethral cancer, urologic tumors, urothelial carcinoma, vulval cancer, wart involvement, soft tissue tumors, soft tissue sarcoma, Wilms tumor, cervical carcinoma, and cancer of the tongue.

Solid tumors are preferred. Moreover, prostate carcinoma, brain tumors, sarcoma, cervical carcinomas, ovarian carcinomas, breast carcinomas, bronchial carcinomas, melanoma, head and neck tumors, esophageal carcinomas, rectal carcinomas, pancreatic, bladder, and renal carcinomas, and metastases of the liver, brain, and lymph nodes are also preferred.

The administration and use of the active substance release system together with conventional hyperthermia, radiotherapy, and/or combined conventional chemotherapy are particularly preferred.

The two components used in an embodiment of the active substance release system according to the invention could be administered by simultaneous or sequential injection.

A preferred embodiment of the present invention concerns medication in which Compounds 1 and 2 are administered to the patient simultaneously or sequentially.

The medication according to the invention can be configured so that Compounds 1 and 2 are administered simultaneously or sequentially, i.e. packaged in the form of a kit as separate products, and implanted in the patient, specifically by intratumoral, interstitial, or intraperitoneal injection. As a rule, both administration schedules are possible. One possibility is to administer Compound 2 containing the active substance at an earlier point in time, and then inject Compound 1 later, followed by heating (as described above) to cleave and thus activate the substance. Conversely, however, one can first implant a depot of Compound 1 in the patient and then later administer Compound 2 with the active substance, in multiple administrations if necessary, after which the substance can be specifically released by the above-mentioned heating. This is possible because the nanoparticles of Compound 1 can remain at one location in the body for years, so the active substance can be repeatedly activated over a period of several years by repeated cleavage of small amounts of catalytic nucleic acids.

For oncological use, the medication according to the invention containing Compound 1 and/or Compound 2 should preferably be placed in the tumor bed and/or the resection hollow when a tumor is removed.

Thus in a further preferred embodiment, the present invention concerns a medication in which Compounds 1 and 2 are placed in the tumor bed when a tumor is removed.

A further object of the present invention is a process for the release of an active substance from Compound 2 as described above comprising the following steps:
(i) Placement of Compound 1 as described above in the vicinity of Compound 2 under conditions that allow diffusion of the released, catalytically active nucleic acid to the substrate oligonucleotide, as well as cleavage thereof, and
(ii) active or passive heating of Compound 1 as described above so that the catalytically active nucleic acid is released.

FIGURES

FIG. 1: Shows cleavage of the fluorescent dye Alexa-647, which serves as a model substance for any desired active substance, by means of the active substance release system according to the invention. The middle curve (-●-) shows the increase in fluorescence in the reaction supernatant due to free Alexa-647, which is released from the nanoparticle-active substance conjugates after activation of the catalytically active RNA sequence by dehybridization at 49° C. The second curve from below (-▲-) shows that at 37° C., dehybridization does not occur, because the increase in fluorescence intensity in the supernatant can be detected. The lower curve (-■-) shows the negative control without the presence of a catalytic nucleic acid. The upper curve (-◆-) shows the positive control, in which the nanoparticle-active substance conjugates were incubated with the non-inhibited catalytically active RNA single strand.

FIG. 2: Shows an embodiment of the active substance release system according to the invention in which the catalytically active nucleic acid and the substrate oligonucleotide to be cleaved with the active substance are bonded to two different nanoparticles. The nanoparticle, with its coating of silicon dioxide, is shown as a ball on the left in each case. Via a linker, the oligonucleotide inhibition strand is bonded to the nanoparticle, and the catalytically active nucleic acid is hybridized with the oligonucleotide inhibition strand. In the middle one can see the nanoparticle, to which the substrate oligonucleotide is bonded via a linker, with said nanoparticle bonded to the active substance (shown as a star) at its other terminal. After this, the accumulation of the released catalytically active nucleic acid on the substrate oligonucleotide is shown, and finally, the cleaved substrate oligonucleotide, which has released the active substance, is shown. Figure discloses SEQ ID NOS 1, 4, 4, 1, 1, 3, 3, 1, and 5, respectively, in order of appearance.

Figure 3:
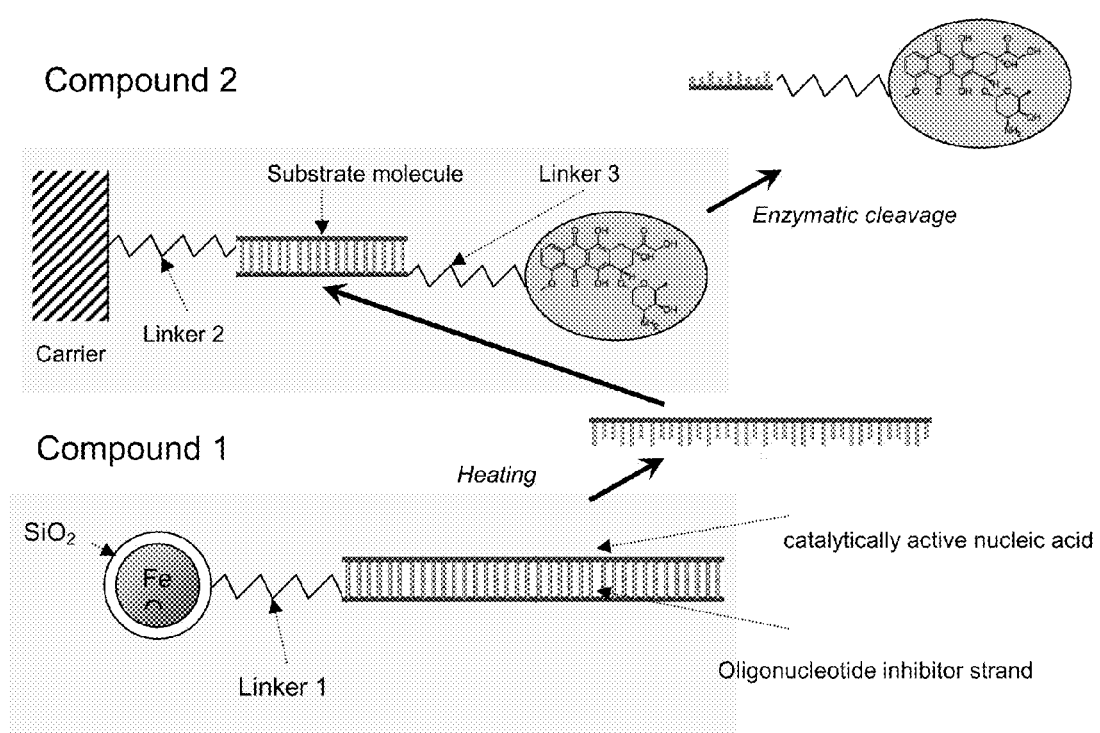

FIG. 3: Schematic diagram of the active substance release systems. The system consists of Compounds 1 and 2, with heating leading to dehybridization of the oligonucleotide inhibitor strand and catalytic activation of the nucleic acid, which is now released and can enzymatically cleave its substrate molecule. This cleavage in turn releases the therapeutically active substance of Compound 2, thus activating it.

Figure 4:
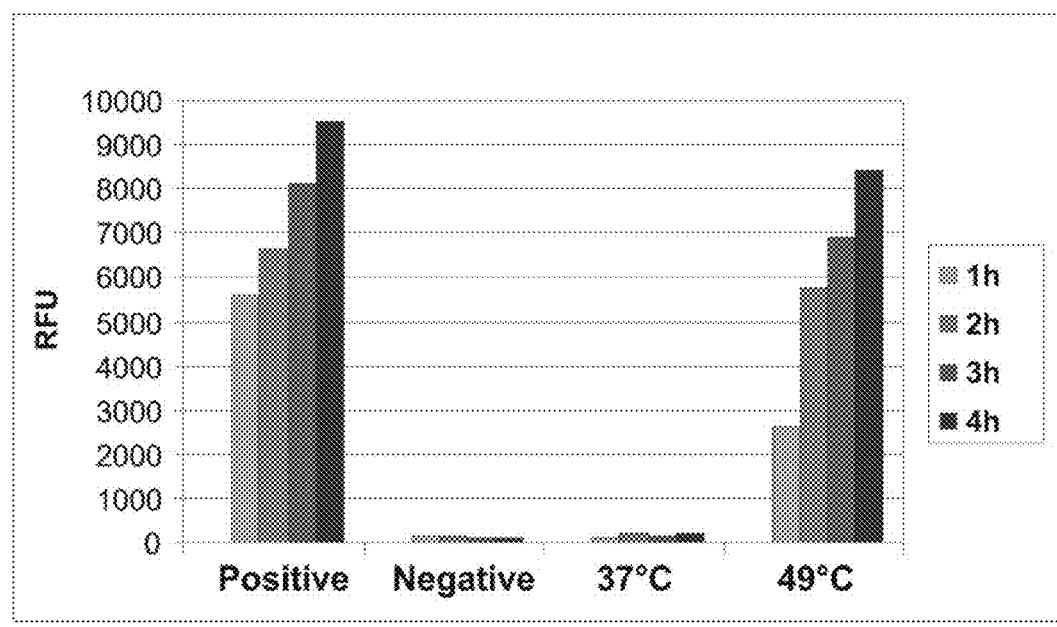

FIG. 4: Temperature-dependent release of the fluorescent dye A-647 coupled to the substrate oligonucleotide by nanoparticle/(L)-substrate oligonucleotide conjugates in the presence of a nanoparticle/(L)-oligonucleotide inhibition strand/ribozyme conjugates in buffer. The RFU in the supernatant was measured after 1, 2, 3, and 4 h incubation at 37°

C. and/or 49° C. Nanoparticle/(L)-substrate oligonucleotide conjugates with free L-ribozymes were used as a positive control, and only nanoparticle/(L)-substrate oligonucleotide conjugates with reaction buffer were used as a negative control.

Figure 5:
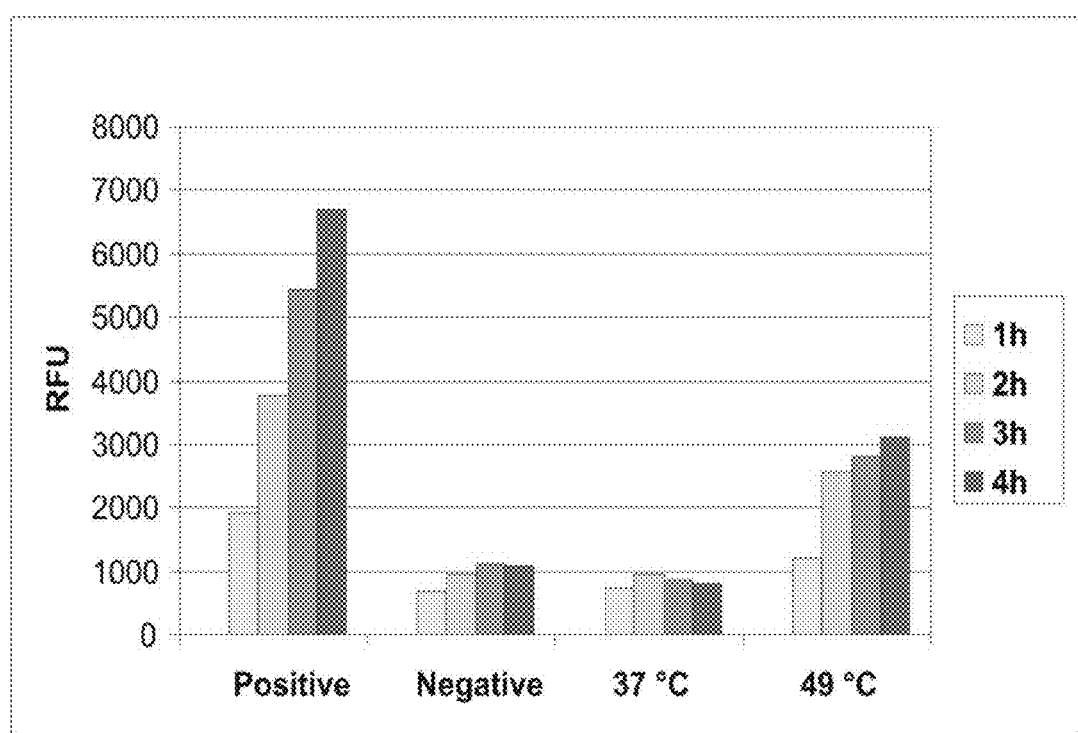

FIG. 5: Temperature-dependent release of the fluorescent dye A-647 coupled to the substrate oligonucleotide by nanoparticle/(L)-substrate oligonucleotide conjugates in the presence of a nanoparticle/(L)-oligonucleotide inhibition strand/ribozyme conjugate in human serum. The RFU in the supernatant was measured after 1, 2, 3 and 4 h incubation at 37° C. and/or 49° C. Nanoparticle/(L)-substrate oligonucleotide conjugates with free L-ribozymes were used as a positive control, and only nanoparticle/(L)-substrate oligonucleotide conjugates with reaction buffer were used as a negative control.

Figure 6:
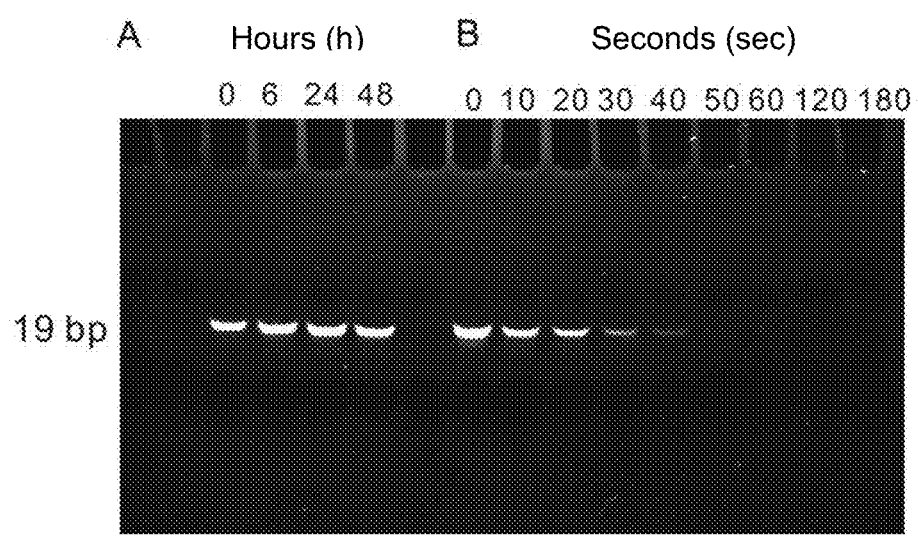

FIG. 6: Stability of L- and R-ribozyme in serum. 30 pmol aliquots of the respective ribozymes with a length of 19 bp were analyzed for breakdown after incubation in human serum at 37° C. for the indicated time. Breakdown of the 19 bp RNA was visualized under UV light in 15% denaturing polyacrylamide gel after dyeing with EtBr. Part A shows the breakdown within 0-48 h for the L-ribozyme, and Part B shows the breakdown within 0-180 sec for the R-ribozyme.

EXAMPLES

Example 1

Temperature-Dependent Cleavage of the Fluorescent Dye Alexa-647 by Catalytic Nucleic Acids Example 1 shows temperature-dependent cleavage of the fluorescent dye Alexa-647 (which serves as a model substance for any desired active substance) by means of the system described above. The catalytic nucleic acid is a ribozyme having the sequence: 5'-GGC UCG ACU GAU GAG GCG C-3' (SEQ ID NO: 1), hybridized to an inhibitor having the sequence: 5'-G CCT CAT CAG TCG AGC C-3' (SEQ ID NO: 2), wherein the 5'-terminal nucleotide carries an SH-group. The double-stranded RNA is bonded via the SH-group and a sulfo-SMCC crosslinker to an amino group of the iron oxide-nanoparticles having an iron oxide core, an $SiO_2$ covering, and DIAMO surface functionalization.

The nanoparticle-active substance conjugate consists of the substrate oligonucleotide and covalently bonded Alexa-647 (model substance, obtained in bonded form from the firm IBA, Göttingen) having the sequence: 5'-GCG CCG AAA CAC CGU GUC UCG AGC-3' (SEQ ID NO: 3), wherein the 5'-terminal nucleotide carries an SH-group and is bonded via the SH-group and a sulfo-SMCC crosslinker to an amino group of the iron oxide nanoparticle having an iron oxide core, an $SiO_2$ covering, and DIAMO surface functionalization.

The heating periods during the experiments are shown in FIG. 1 as bars. The middle curve (-●-) shows the increase in fluorescence in the reaction supernatant due to free Alexa-647, which is released from the nanoparticle-active substance conjugates after activation of the catalytically active RNA sequence by dehybridization at 49° C. At 37° C. (second curve from below: -▲-), as dehybridization does not occur and the ribozyme remains inhibited, no increase in fluorescence intensity is detected in the supernatant. The nanoparticle-active substance conjugate (NP-crosslinker-substrate strand with Alexa-647) in the absence of a catalytic nucleic acid was used as a negative control (lower curve: -■-). The nanoparticle-active substance conjugate was incubated with the non-inhibited catalytically active RNA single strand as a positive control (upper curve: -♦-).

Example 2

Nanoparticle-Nucleic Acid Coupling with Sulfo-SMCC

Using the same method as in Example 1, sulfo-SMCC was used as a linker for coupling between 5'-terminal-thiol-group-modified oligonucleotide in the L-form and iron oxide nanoparticles. This was carried out for the substrate oligonucleotide and the oligonucleotide inhibition strand/ribozyme-double strand, which were hybridized before coupling at a molar ratio of 1.1:1 in PBS (pH 6.7).

TABLE 1

| Nucleotides used in L-Form | | |
|---|---|---|
| Ribozyme | L-RNA | 5'-GGC UCG ACU GAU GAG GCG C-3' SEQ ID NO: 1 |
| Oligo-inhibitor | L-DNA | 5'-G CCT CAT CAG TCG AGC C-3' SEQ ID NO: 2 |
| Substrate oligo | L-RNA | 5'-GCG CCG AAA CAC CGU GUC ↓ UCG AGC-3' SEQ ID NO: 3 |

↓ is the substrate oligonucleotide interface (Ruffner and Uhlenbeck, 1990).

The 15 nm iron oxide nanoparticles contain approx. 550 amine groups per particle. The oligonucleotides were first reduced with 1 mM TCEP (Sigma). For coupling by means of sulfo-SMCC (Sigma), the iron oxide nanoparticles were first reacted with sulfo-SMCC in a Thermomixer for incubation at a concentration of 2.2 mM in PBS (pH 7.4) for 1 h at room temperature and 1000 rpm (revolutions per minute). The excess linkers were separated by centrifugation. The nanoparticles were then washed twice with distilled water. The reduced oligonucleotides were now added at a molar ratio of oligonucleotides to nanoparticle of 65:1 and subjected to rotary incubation in PBS (pH 6.7) at 4° C. overnight. The non-conjugated oligonucleotides were separated by centrifugation.

Example 3

Release Experiments with the Ribozyme-Nanoparticle-Active Substance Release System Nanoparticle/(L)-substrate oligonucleotide* conjugates and nanoparticle/(L)-oligonucleotide inhibition strand/ribozyme conjugates were produced as described in Example 2. The release experiments were carried out in reaction buffer and human serum.

A. In Reaction Buffer:

The conjugates produced in Example 2 were resuspended in reaction buffer (Tris-HCl 50 mM, pH 7.5, with 10 mM $MgCl_2$) and mixed in a 1:1 ratio in 1.5 ml reaction vessels (two batches, for 37° C. and 49° C.). As a positive control, nanoparticle/(L)-substrate oligonucleotide conjugates with 0.625 μM of the free L-ribozyme were prepared in reaction buffer with a sequence identical to that shown in Table 1. Corresponding nanoparticle/(L)-substrate oligonucleotide conjugates were mixed with reaction buffer and used as a negative control. All four reaction batches had the same final concentration of the nanoparticle/(L)-substrate oligonucleotide-conjugate.

One batch of the conjugates was incubated at 37° C. and the other at 49° C. in a Thermomixer for 1-4 h. Both controls were incubated at both 37° C. and 49° C., and no significant differences were observed. Aliquots of each batch were taken after 1, 2, 3 and 4 h and immediately centrifuged. The supernatant was carefully poured into a new reaction vessel. The RFU (relative fluorescence unit) intensity of the supernatant was measured with a NanoDrop 3300 fluorospectrometer (Thermo Scientific).

The fluorescence signal at 49° C. showed clear time-dependent release of the fluorescent dye, which almost reached the level of the positive control with increasing incubation. In contrast, virtually no release was seen in the negative control or at 37° C., even after 4 h (see FIG. 4).

B. In Human Serum:

The experiments described under A were repeated in human serum instead of reaction buffer in an incubator at 37° C. and/or 49° C., 94.5% humidity, and 5% $CO_2$.

In human serum as well, clear time-dependent release of the fluorescent dye was observed at 49° C., and in this case, the release due to the ribozyme in the presence of the conjugated inhibitor strand was only about half as strong as that seen for the positive control (in the absence of an inhibitor strand) (see FIG. 5). Moreover, the release of the dye in the negative control and the 37° C. batch was increased with respect to the corresponding batches in buffer (compare FIG. 5 with to FIG. 4).

Example 4

Serum Stability Assay of the R- and/or L-Ribozyme

The stability assays were carried out by essentially the same method as that described by von Klussmann (1996). Human serum S7023 was obtained from is Sigma (USA). The L-ribozyme (see Table 1) and its corresponding R-form (both 19 bp) were incubated at a concentration of 10 μM in 90% human serum in an incubator at 37° C., 94.5% humidity, and 5% $CO_2$ (0 to 6 h for the L-ribozyme, 0 to 180 sec for the R-ribozyme). Aliquots were mixed in a 1:1 ratio with stop solution (8 M urea, 50 mM EDTA, 2% SDS) and immediately frozen in liquid nitrogen. The samples were filtered through a Microcon YM-30 (Millipore) filter, and 30 pmol of RNA each was separated according to size in 15% denaturing polyacrylamide gel (7M urea). The gel was dyed in EtBr-solution (1 μg/ml) for 15 min and photographed under UV light (302 nm).

While the L-ribozyme shows no breakdown, even over 48 h of incubation (Part A of FIG. 6), the R-ribozyme is already undetectable after 120 sec in the EtBr-dyed gel (Part B of FIG. 6).

REFERENCES

ABU AJAJ, K., GRAESER, R., FICHTNER, I. & KRATZ, F. 2009. In vitro and in vivo study of an albumin-binding prodrug of doxorubicin that is cleaved by cathepsin B. *Cancer Chemother Pharmacol.*, 64, 413-8. Epub 2009 Feb. 20.

BOGA, C., FIUME, L., BAGLIONI, M., BERTUCCI, C., FARINA, C., KRATZ, F., MANERBA, M., NALDI, M., DI STEFANO, G., CALDERON, M., GRAESER, R., HAAG, R., ABU AJAJ, K. & FICHTNER, I. 2009. Characterisation of the conjugate of the (6-maleimidocaproyl)hydrazone derivative of doxorubicin with lactosaminated human albumin by 13C NMR spectroscopy; Development of enzymatically cleavable prodrugs derived from dendritic polyglycerol; In vitro and in vivo study of an albumin-binding prodrug of doxorubicin that is cleaved by cathepsin B. *Eur J Pharm Sci.*, 38, 262-9. Epub 2009 Aug. 18.

CALDERON, M., GRAESER, R., KRATZ, F., HAAG, R., ABU AJAJ, K. & FICHTNER, I. 2009. Development of enzymatically cleavable prodrugs derived from dendritic polyglycerol; In vitro and in vivo study of an albumin-binding prodrug of doxorubicin that is cleaved by cathepsin B. *Bioorg Med Chem Lett.*, 19, 3725-8. Epub 2009 May 18.

CARMI, N., BALKHI, S. R., BREAKER, R. R., SUN, L. Q., CAIRNS, M. J., SARAVOLAC, E. G., BAKER, A. & GERLACH, W. L. 1998. Cleaving DNA with DNA; Catalytic nucleic acids: from lab to applications. *Proc Natl Acad Sci USA.*, 95, 2233-7.

KARKARE, S. & BHATNAGAR, D. 2006. Promising nucleic acid analogs and mimics: characteristic features and applications of PNA, LNA, and morpholino. *Appl Microbiol Biotechnol.*, 71, 575-86. Epub 2006 May 9.

KLUSSMANN, S., NOLTE, A., BALD, R., ERDMANN, V. A., FURSTE, J. P., RUFFNER, D. E. & UHLENBECK, O. C. 1996. Mirror-image RNA that binds D-adenosine; thiophosphate interference experiments locate phosphates important for the hammerhead RNA self-cleavage reaction. *Nat Biotechnol.*, 14, 1112-5.

KRATZ, F., BOGA, C., FIUME, L., BAGLIONI, M., BERTUCCI, C., FARINA, C., MANERBA, M., NALDI, M., DI STEFANO, G., CALDERON, M., GRAESER, R., HAAG, R., ABU AJAJ, K. & FICHTNER, I. 2008. Albumin as a drug carrier: design of prodrugs, drug conjugates and nanoparticles; Characterisation of the conjugate of the (6-maleimidocaproyl)hydrazone derivative of doxorubicin with lactosaminated human albumin by 13C NMR spectroscopy; Development of enzymatically cleavable prodrugs derived from dendritic polyglycerol; In vitro and in vivo study of an albumin-binding prodrug of doxorubicin that is cleaved by cathepsin B. *J Control Release.*, 132, 171-83. Epub 2008 May 17.

RUFFNER, D. E. & UHLENBECK, O. C. 1990. Thiophosphate interference experiments locate phosphates important for the hammerhead RNA self-cleavage reaction. *Nucleic Acids Res.*, 18, 6025-9.

SANTORO, S. W., JOYCE, G. F., CARMI, N., BALKHI, S. R., BREAKER, R. R., SUN, L. Q., CAIRNS, M. J., SARAVOLAC, E. G., BAKER, A. & GERLACH, W. L. 1997. A general purpose RNA-cleaving DNA enzyme; Cleaving DNA with DNA; Catalytic nucleic acids: from lab to applications. *Proc Natl Acad Sci USA.*, 94, 4262-6.

SEELIG, B., KEIPER, S., STUHLMANN, F. & JASCHKE, A. 2000. Enantioselective ribozymes: Catalysis of a Bimolecular Cycloaddition Reaction. This work was supported by the Deutsche Forschungsgemeinschaft (Grant no.: Ja 794/3-1) and the Federal Ministry of Education and Research (Grant no.: BEO 0311861). We thank Dr. S. Klussmann and Dr. S. Vonhoff (Noxxon Pharma AG, Berlin) for the synthesis of the L-ribozyme. *Angew Chem Int Ed Engl.*, 39, 4576-4579.

ZHANG, S. & CHAPUT, J. C. 2010. Synthesis of glycerol nucleic acid (GNA) phosphoramidite monomers and oligonucleotide polymers. *Curr Protoc Nucleic Acid Chem.* Chapter, Unit 4.40.

Preferred embodiments are:
1. An active substance release system, comprising a nanoparticle bonded to an oligonucleotide inhibitor strand that is hybridized with a catalytically active nucleic acid, and a further nanoparticle bonded to a substrate oligonucleotide that is bonded to a therapeutically active substance, which can be released through cleavage of the substrate oligonucleotide by the catalytically active nucleic acid.
2. An active substance release system according to 1, wherein the oligonucleotide inhibitor strand is bonded to the nanoparticle via a crosslinker.
3. An active substance release system according to 1 or 2, wherein the substrate oligonucleotide is bonded to the nanoparticle via a crosslinker.
4. An active substance release system according to 1 to 3, wherein at least one therapeutically active substance is selected from the group comprising antiproliferative, antimigrative, anti-angiogenic, antithrombotic, anti-inflammatory, antiphlogistic, cytostatic, cytotoxic, anticoagulant, antibacterial, antiviral and/or antimycotic active substances, opioid agonists, non-opioid analgesics, non-steroidal anti-inflammatories (NSAIDs), anti-migraine agents, cox-II inhibitors, β-adrenergic blockers, anticonvulsants, antidepressants, $Ca^{2+}$ channel blockers, or active substances for the treatment of neuronal or neurodegenerative diseases.
5. An active substance release system according to 4, wherein at least one therapeutically active substance is selected from the group comprising actinomycin D, aminoglutethimide, amsacrine, anastrozole, purine and pyrimidine base antagonists, anthracyclines, aromatase inhibitors, asparaginase, antiestrogens, bexarotene, bleomycin, buserelin, busulfan, camptothecin derivatives, capecitabine, carboplatin, carmustine, chlorambucil, cisplatin, cladribine, cyclophosphamide, cytarabine, cytosine arabinoside, alkylating cytostatics, dacarbazine, dactinomycin, daunorubicin, docetaxel, doxorubicin (Adriamycin), doxorubicin Lipo, epirubicin, estramustine, etoposide, exemestane, fludarabine, fluorouracil, folic acid antagonists, formestane, gemcitabine, glucocorticoids, goserelin, hormone and hormone antagonists, hycamtin, hydroxyurea, idarubicin, ifosfamide, imatinib, irinotecan, letrozole, leuprorelin, lomustine, melphalan, mercaptopurine, methotrexate, miltefosine, mitomycin, mitosis inhibitors, mitoxantrone, nimustine, oxaliplatin, paclitaxel, pentostatin, procarbazine, tamoxifen, temozolomide, teniposide, testolactone, thiotepa, thioguanine, topoisomerase inhibitors, topotecan, treosulfan, tretinoin, triptorelin, trofosfamide, vinblastine, vincristine, vindesine, vinorelbine, and cytostatically active antibiotics.
6. An active substance release system according to 4, wherein at least one therapeutically active substance is selected from the group comprising nucleic acids, siRNA, amino acids, peptides, proteins, carbohydrates, lipids, glycoproteins, glycans, or lipoproteins, wherein said substances possess antiproliferative, antimigrative, anti-angiogenic, antithrombotic, anti-inflammatory, antiphlogistic, cytostatic, cytotoxic, anticoagulant, antibacterial, antiviral and/or antimycotic properties.
7. Use of the active substance release systems according to 1 to 6 for the production of a pharmaceutical compound for the treatment and/or prevention of proliferative diseases, cancer and bacterial infections.
8. A nanoparticle that is bonded to an oligonucleotide inhibitor strand that is hybridized with a catalytically active nucleic acid, which is capable of cleaving a substrate oligonucleotide that is bonded to a further nanoparticle and the therapeutically active substance.
9. A nanoparticle that is bonded to a therapeutically active substance and a substrate oligonucleotide, wherein the substrate oligonucleotide can be cleaved by a catalytically active nucleic acid.

The invention claimed is:

1. An active substance release system, containing
   i) a Compound 1, containing at least one nanoparticle bonded to an oligonucleotide inhibitor strand, wherein said oligonucleotide inhibitor strand is hybridized with a catalytically active nucleic acid which upon dehybridization and release is catalytically active for specifically cleaving a substrate molecule in a Compound 2 which is also part of the active substance release system, and
   ii) the Compound 2, containing a carrier bonded to at least one substrate molecule which is specifically cleaved by the catalytically active nucleic acid from Compound 1, wherein the substrate molecule is bonded to at least one therapeutically active substance,
   wherein the therapeutically active substance can be released by the specific cleavage of the substrate molecule, with the substrate molecules being specifically cleaved by the catalytically active nucleic acid.

2. The active substance release system as claimed in claim 1, wherein the oligonucleotide inhibitor strand is covalently bonded to the nanoparticle.

3. The active substance release system as claimed in claim 1, wherein the catalytically active nucleic acid and the oligonucleotide inhibitor strand are selected from the group consisting of RNA, DNA, L-RNA, L-DNA, and a modified nucleic acid.

4. The active substance release system as claimed in claim 2, wherein the oligonucleotide inhibitor strand is covalently bonded via a Linker 1 to the nanoparticle; wherein Linker 1 is formed on the 5'-terminal of the oligonucleotide inhibitor strand.

5. The active substance release system as claimed in claim 1, wherein in Compound 1, the ratio of the oligonucleotide inhibitor strands to the catalytically active nucleic acid is ≥1.

6. The active substance release system as claimed in claim 3, wherein in Compound 1, the ratio of the oligonucleotide inhibitor strands to the catalytically active nucleic acid is 1.0 to 1.3.

7. The active substance release system as claimed in claim 1, wherein the catalytically active nucleic acid is completely hybridized with the oligonucleotide inhibitor strand under physiological conditions, and in which at 43° C., at least one catalytically active nucleic acid is dehybridized.

8. The active substance release system as claimed in claim 1, wherein the nanoparticle possesses a core containing at least a paramagnetic or superparamagnetic iron oxide.

9. The active substance release system as claimed in claim 8, wherein the therapeutically active substance is released by cleavage of the substrate molecule, with the substrate molecules being cleaved by the catalytically active nucleic acid, when the paramagnetic or superparamagnetic nanoparticles are heated in an alternating magnetic field.

10. The active substance release system as claimed in claim 1, wherein the nanoparticle has at least one covering.

11. The active substance release system as claimed in claim 1, wherein the substrate molecule is an oligonucleotide.

12. The active substance release system as claimed in claim 1, wherein the carrier is a polymer, an $SiO_2$ particle, or a metallic particle, which is present in the form of a gel, microparticles, microspheres, or nanoparticles.

13. The active substance release system as claimed in claim 1, wherein the substrate molecule is bonded covalently.

14. The active substance release system as claimed in claim 11, wherein the substrate molecule oligonucleotide is selected from the group consisting of DNA, RNA, L-DNA, L-RNA, and a modified nucleic acid.

15. The active substance release system as claimed in claim 14, wherein the substrate molecule oligonucleotide has a length of 10 to 100 nucleotides.

16. The active substance release system as claimed in claim 1, wherein the therapeutically active substance is selected from the group consisting of nucleic acids, siRNAs, antisense RNAs, amino acids, aptamers, peptides, proteins, glycoproteins, carbohydrates, glycans, lipids, and lipoproteins.

17. The active substance release system as claimed in claim 1, wherein the therapeutically active substance is covalently bonded to the substrate molecule.

18. The active substance release system as claimed in claim 17, wherein the therapeutically active substance is covalently bonded to the substrate molecule via a Linker 3, wherein Linker 3 is selected from the group consisting of an amino group and hydrazone.

19. The active substance release system as claimed in claim 17, wherein the therapeutically active substance is inactive as long as it is bonded to the substrate molecule, and it is activated when the therapeutically active substance is released from the substrate molecule, or after subsequent intake into a cell.

20. The active substance release system as claimed in claim 1, wherein the catalytically active nucleic acid can cleave the substrate molecule, provided that the catalytically active nucleic acid is dissociated from the oligonucleotide inhibitor strand, wherein the following applies in the cleavage reaction of the substrate molecules via the catalytically active nucleic acid: the concentration of the substrate molecules is $\geq KM$.

21. The active substance release system as claimed in claim 1, wherein the ratio of Compound 1 to Compound 2 is $\leq 2$.

22. The active substance release system as claimed in claim 11, wherein the oligonucleotide inhibitor strand, the catalytically active nucleic acid, and the substrate oligonucleotide are all mirror-image nucleic acids.

23. A medicine containing an active substance release system as claimed in claim 1.

24. A medicine containing an active substance release system as claimed in claim 1 for the treatment and/or prevention of proliferative diseases, cancer, inflammatory diseases, autoimmune diseases, and bacterial infections.

25. The medicine as claimed in claim 24, wherein Compounds 1 and 2 are adapted in the release system to be administered to the patient simultaneously or sequentially.

26. The medicine as claimed in claim 24, wherein Compounds 1 and 2 are adapted in the release system to be placed in the tumor bed when a tumor is removed.

27. A process for the release of an active substance from Compound 2 as claimed in claim 1, comprising the following steps:
  i) placement of Compound 1 as described in claim 1 in the vicinity of Compound 2 under conditions that allow diffusion of the released, catalytically active nucleic acid to the substrate oligonucleotide, as well as cleavage thereof, and
  (ii) active or passive heating of Compound 1 so that the catalytically active nucleic acid is released.

28. The active substance release system as claimed in claim 1, wherein the therapeutically active substance is a substance having an antiproliferative, cytostatic, cytotoxic, antimigrative, anti-angiogenic, antithrombotic, anti-inflammatory, anti-phlogistic, anticoagulant, antibacterial, antiviral and/or antimycotic action.

29. The active substance release system as claimed in claim 20, wherein $k_{cat}$ is $\geq 0.05$ min.

30. The active substance release system as claimed in claim 1, wherein the therapeutically active substance is a low-molecular-weight therapeutically active substance.

* * * * *